US007998757B2

(12) United States Patent
Darrigrand et al.

(10) Patent No.: US 7,998,757 B2
(45) Date of Patent: Aug. 16, 2011

(54) CONTAINER AND METHOD FOR SUPPORTING HOME TESTING AND DIAGNOSIS OF INFECTIOUS DISEASES

(75) Inventors: William A. Darrigrand, Nazareth, PA (US); P. Michael Formica, Center Valley, PA (US); Charles Zunda, Historic South Norwalk, CT (US); Jared Alden Judson, Topsfield, MA (US); Devorah Emily Klein, Cambridge, MA (US); Gian A. Pangaro, Boston, MA (US); Jason Robinson, Tewksbury, MA (US)

(73) Assignee: Orasure Technologies, Inc., Bethlehem, PA (US)

( * ) Notice: Subject to any disclaimer, the term of this patent is extended or adjusted under 35 U.S.C. 154(b) by 179 days.

(21) Appl. No.: 12/017,901

(22) Filed: Jan. 22, 2008

(65) Prior Publication Data

US 2009/0004055 A1    Jan. 1, 2009

Related U.S. Application Data

(60) Provisional application No. 60/881,492, filed on Jan. 22, 2007, provisional application No. 60/911,186, filed on Apr. 11, 2007, provisional application No. 60/911,192, filed on Apr. 11, 2007.

(51) Int. Cl.
| | |
|---|---|
| *G01N 15/06* | (2006.01) |
| *G01N 33/00* | (2006.01) |
| *G01N 33/48* | (2006.01) |
| *G01N 21/75* | (2006.01) |
| *G01N 31/22* | (2006.01) |
| *G01N 33/52* | (2006.01) |
| *B01L 3/00* | (2006.01) |
| *B01L 99/00* | (2010.01) |
| *B01L 31/22* | (2006.01) |
| *B01L 33/52* | (2006.01) |

(52) U.S. Cl. ........ 436/808; 436/807; 422/68.1; 422/401; 422/430; 422/500

(58) Field of Classification Search .................... 422/61; 434/298; 206/579, 569
See application file for complete search history.

(56) References Cited

U.S. PATENT DOCUMENTS

| 4,195,059 A | 3/1980 | Whitcher et al. | |
|---|---|---|---|
| 5,100,621 A * | 3/1992 | Berke et al. | ..................... 422/61 |

(Continued)

OTHER PUBLICATIONS

International Search Report mailed May 20, 2008, International Application No. PCT/US08/00769.

*Primary Examiner* — Jill Warden
*Assistant Examiner* — Charles Hammond
(74) *Attorney, Agent, or Firm* — J.A. Lindeman & Co., PLLC

(57) ABSTRACT

A container is configured to provide sequential access to contents therein, and includes an upper portion and a lower portion connected to the upper portion by a hinged portion, the lower portion defining an interior space bearing a moveable tray and an opening through which the moveable tray may move, the moveable tray defining an interior volume configured to receive at least one device therewithin. The container also includes at least one device borne by the moveable tray, at least one cavity for receiving the at least one device disposed in the upper portion and at least one insert located between the upper and lower portions, the at least one insert comprising at least written indicia thereon.

5 Claims, 31 Drawing Sheets

U.S. PATENT DOCUMENTS

| | | | |
|---|---|---|---|
| 5,207,303 A | | 5/1993 | Oswalt et al. |
| 5,353,803 A | * | 10/1994 | Cerra ............................ 600/562 |
| 5,791,487 A | * | 8/1998 | Dixon ............................ 206/758 |
| 5,878,757 A | * | 3/1999 | Hernandez .................... 206/349 |
| 6,781,522 B2 | | 8/2004 | Sleva et al. |
| 2004/0052684 A1 | * | 3/2004 | Sinsky et al. ................... 422/61 |
| 2006/0293577 A1 | * | 12/2006 | Morrison et al. ............. 600/365 |

* cited by examiner

| 1 & 2 | 3 & 4 | 5 |

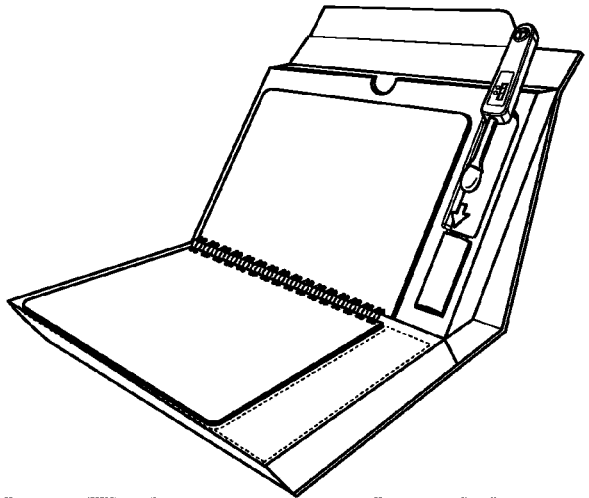

5 Drop In & Start Timing    Gota Adentro y Commence

Drop In & Start Timing
- Put the test stick directly into the test tube flat pad first. Make sure the test stick window is facing you.
- NOTE: Do not take test stick out of the test tube early or your results will be wrong.
- Write down your Start Time as directed on the page below.

Gota Adentro
- Puso el palo de la prueba directamente en la probeta almohadilla plana primero. Cerclórese la ventana del palo de la prueba está frente a usted.
- NOTA: No tome el palo de la prueba fuera de la probeta tempranos ni sus resultados eslará equivocado.
- Escrive su Hora de Salida como indicado su la Pagina abajo.

FIG. 15

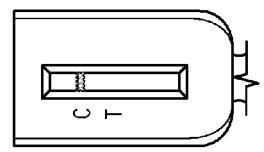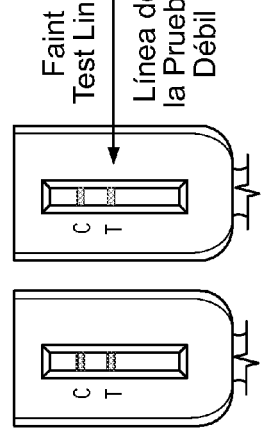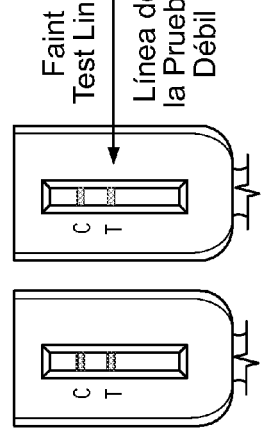
FIG. 19

US 7,998,757 B2

CONTAINER AND METHOD FOR SUPPORTING HOME TESTING AND DIAGNOSIS OF INFECTIOUS DISEASES

CROSS REFERENCE TO RELATED APPLICATIONS

This application claims the benefit of priority of U.S. Provisional Patent Application No. 60/881,492, filed on Jan. 22, 2007, U.S. Provisional Patent Application No. 60/911,186, filed Apr. 11, 2007, and U.S. Provisional Patent Application No. 60/911,192, filed Apr. 11, 2007, all of which are incorporated herein by reference in their entirety.

BACKGROUND OF THE INVENTION

1. Field of the Invention

The present invention relates to a container and method for home testing and diagnosis of infectious diseases, including HIV and hepatitis C, and more particularly to a container that provides sequential access to the articles or goods contained therein to increase testing compliance and correct usage.

2. Description of the Related Art

Self testing kits for various diseases and/or physiological conditions have increased in popularity. In such kits, the user typically obtains a sample of physiological fluid, for example, blood, urine, saliva, etc., and introduces the sample into a home test system that produces a coded pattern indicative of the presence or absence of the disease or condition.

A problem with the emergence of these over-the-counter (OTC) medical devices, self delivery drug devices, as well as other testing products, is that they require detailed use and instructions to be accurately used by the user. Although the manufacturer may provide carefully written instructions and warnings, users often access and use the device or product housed within the container without ever considering such instructions. As a result, the effectiveness of the test may be reduced when the test is incorrectly administered by a consumer as opposed to a trained professional. Effective and correct use of the test can determine whether ever increasing performance specifications required by the FDA are successfully met.

Furthermore, the installation and use instructions for such products and devices are often complex and presented on multiple pages in pamphlet form. It is easy for the user to ignore or lose instructions provided in this form.

More often, OTC medical devices, self delivery drug devices and other medical testing devices have multiple components that need to be administered, assembled, or installed in a particular order and performance may be highly dependent on timing parameters. Despite detailed instructions and indicia, users often misunderstand the sequence or timing requirements, resulting in improper assembly, installation, or use. As a result, the products are often rendered ineffective. U.S. Pat. No. 6,382,205, for example, discloses a packaged medical device complete with instructions for use. However, the user has the ability to access the different components independent of the instructions, making it easy for the user to remove the components without ever reading the instructions.

Accordingly, there is a need for a method and/or container or package for testing devices and products that compels or encourages the user to read detailed use-instructions prior to using, assembling, or interpreting the devices/and or products.

There is a further need to provide an improved method of packaging such testing devices and components, whereby the user must first access the instructions or other vital information before the user can access the device or product.

There is also a need for a method and/or container that provides information on how the user can access interactive guidance or counseling regarding that tells the user how to use the test, interpret the results, and/or take appropriate steps for prevention or treatment after administering the test.

SUMMARY OF THE INVENTION

The present invention overcomes the disadvantages of the prior art by providing a container or package that assists the consumer in considering use of the devices, and encourages compliance by the user such that the instructions must be removed prior to accessing the device or component discouraging the user from racing through the information.

Another aspect of the present invention is to provide a method of packaging a device or component that limits access to the device or product until the instructions or other information are first removed.

Still another aspect of the present invention is to provide a container or package that provides sequential access to the product or device such that a prescribed number of layers of material must be accessed prior to reaching the product or device. Such layers of material provide ample room for sequential instruction sheets.

It is yet a further aspect of the present invention to provide a method to package a device or component to prevent tampering and/or contamination.

The present invention also aids assembly of multi-part devices by allowing sequential access to the parts in prescribed steps.

Another aspect of the invention provides pre-test and/or post-test counseling to users.

In accordance with the present invention there is provided a container having sequential access to contents therein. The container includes an upper portion and at least one cavity for receiving at least one device located in the upper portion. An inner cover removably covers access to the at least one cavity and includes written indicia. A lower portion is connected to the upper portion and includes at least one recess for receiving at least one article. At least one insert is located between the upper and lower portions, wherein the at least one insert is located above the at least one recess and includes written indicia thereon.

In one optional aspect of the above described container, the container may further comprise a bottom cover covering the at least one recess. In other optional aspects, written indicia may be provided on the inner cover and at least one insert may include instructions and/or warnings for use of the device. In another optional aspect, written indicia may be provided on at least one insert, including sequential instructions for use of the at least one device. In other optional aspects, the at least one cavity includes a plurality of chambers, each of the chambers receiving a component of the device. This latter aspect may further comprise at least one subsequent insert removably disposed in the at least one recess and this at least one subsequent insert may further optionally include written information.

In yet another optional aspect of the above described container, the noted at least one device may comprise a testing device for the testing and diagnosis of infectious diseases. In accord with this aspect, the written indicia on the cover may include information regarding the type of testing device and/or the written indicia on the at least one insert includes sequential instructions for assembling and using the testing device and determining a test result. In yet another optional aspect of the above described container, the inner cover includes a flap that covers the access to the at least one cavity. In still another optional aspect of the above described container, the container further comprises an outer cover located above the inner cover. In various aspects thereof, the outer cover includes written indicia on an inside thereof. These written indicia may include instructions and/or warnings for use of the device.

In accordance with the present invention there is also provided a method of providing sequential access to devices or articles located within a container including the steps of providing a container, the container including an upper portion with at least one cavity for receiving at least one article or device, an inner cover removably covering access to the at least one cavity, the cover including written indicia, and a lower portion connected to the upper portion. The lower portion includes at least one recess for receiving at least one article. An article or device is positioned in the at least one cavity. Access to the at least one cavity is covered by the inner cover. At least one article or device is positioned in the at least one recess. At least one removable insert is positioned between the upper and lower portions, wherein the at least one insert is located above the at least one recess. The at least one recess is covered by the at least one removable insert, wherein the insert must first be removed, sequentially followed by any subsequent inserts before the article or device can be retrieved from the at least one recess.

In various optional aspects of the above described method, the method may further comprise the act of providing written indicia from the group of instructions, warnings or diagrams on the inner cover and at least one insert. The act of providing written indicia may itself optionally comprise beginning the instructions, warnings or diagrams on the inner cover and continuing the same sequentially in the insert. The noted article or device is optionally a testing device for the testing and/or diagnosis of infectious diseases and the act of positioning at least one article or device in the at least one cavity comprises positioning components of the testing device in the cavity. In another optional aspect, the written indicia on the at least one insert includes sequential instructions for assembling and using the testing device and determining a test result.

In yet another aspect, a testing kit is configured to provide sequential access to contents therein, the testing kit including an upper portion, a lower portion connected to the upper portion by a hinged portion, the lower portion defining an interior space bearing a tray and an opening through which the tray may be accessed, the tray defining an interior volume configured to receive a plurality of test components therewithin. The testing kit also includes a plurality of test components borne by the tray, the plurality of test components collectively enabling the performance of at least one test, at least one cavity formed in the upper portion for receiving at least one of the plurality of test components, and at least one instructional insert disposed between the upper portion and the lower portion.

In still another aspect, the present concepts include a method of providing sequential access to devices or articles located within a container, comprising the act of providing a container, the container including an upper portion with at least one cavity for receiving at least one article or device, a lower portion connected to the upper portion, an instructional insert disposed between the upper portion and the lower portion, a moveable tray disposed in the lower portion, and a plurality of articles disposed in the tray. The method also includes the acts of accessing at least one instruction in the instructional insert, accessing an article disposed in the tray in correspondence to the instructions in the instructional insert, and performing an act directed by the instructions in the instructional insert utilizing the article disposed in the tray in correspondence to the instructions in the instructional insert, and determining a test result.

In another aspect of the present concepts, a container is configured to provide sequential access to contents therein, and includes an upper portion and a lower portion connected to the upper portion by a hinged portion, the lower portion defining an interior space bearing a moveable tray and an opening through which the moveable tray may move, the moveable tray defining an interior volume configured to receive at least one device therewithin. The container also includes at least one device borne by the moveable tray, at least one cavity for receiving the at least one device disposed in the upper portion and at least one insert located between the upper and lower portions, the at least one insert comprising at least written indicia thereon.

In still other aspects of the present concepts, a pre-test counseling and/or post-test counseling is provided in combination with any of the above aspects, the counseling being provided via website to any user having access to any internet-ready processing device and/or via telephone to any user having access to a phone.

Other features, aspects and advantages of the present invention will be apparent from the following specification, drawings and claims.

BRIEF DESCRIPTION OF THE DRAWINGS

FIG. 15 illustrates the written instructions for the placement of the used device back in the container.

FIG. 19 illustrates the sequential instructions for determining the test results.

DETAILED DESCRIPTION OF THE PREFERRED EMBODIMENTS

Figure 1:
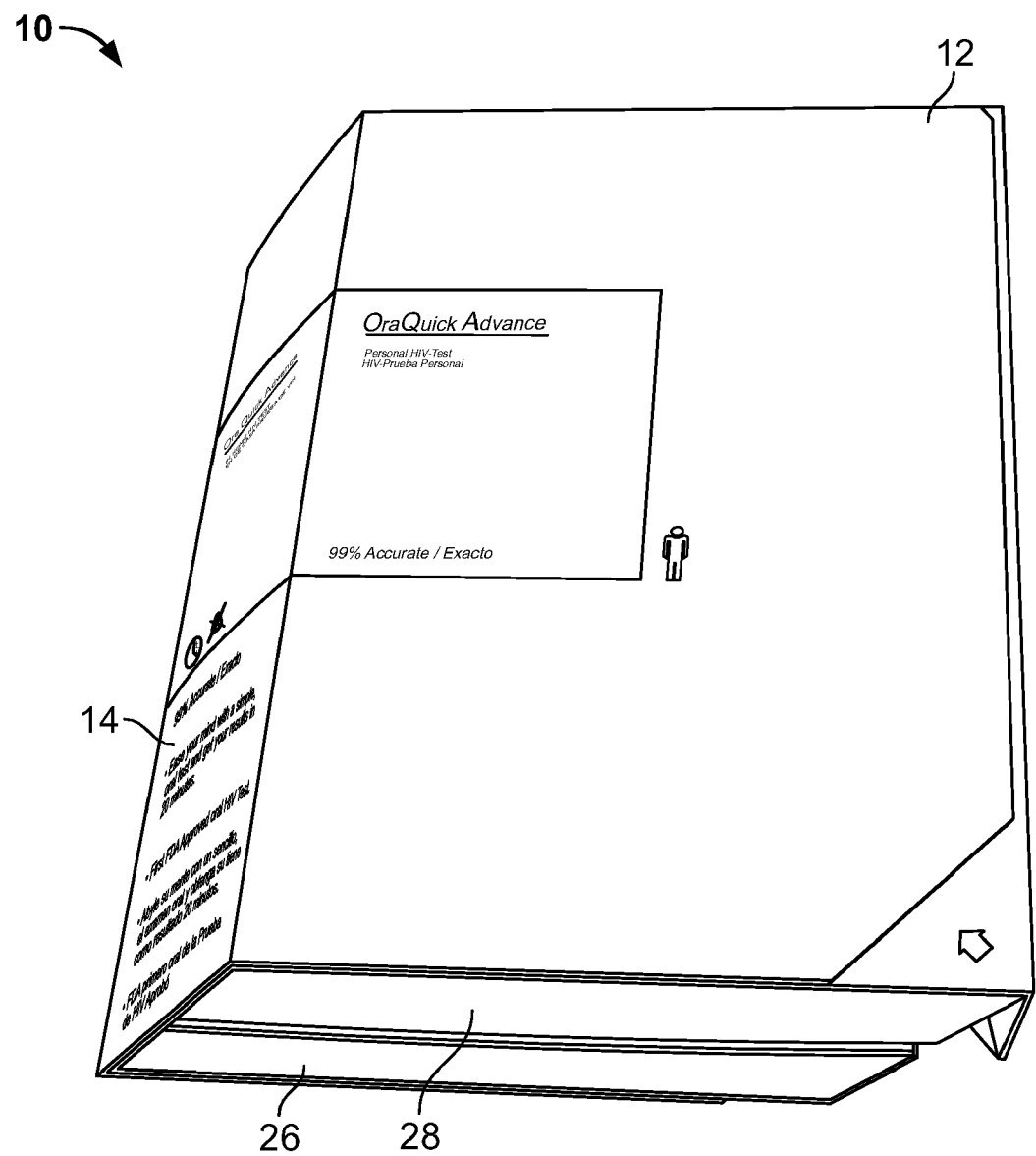
FIG. 1 is a perspective view of the testing container according to aspects of the present invention.
Figure 2:
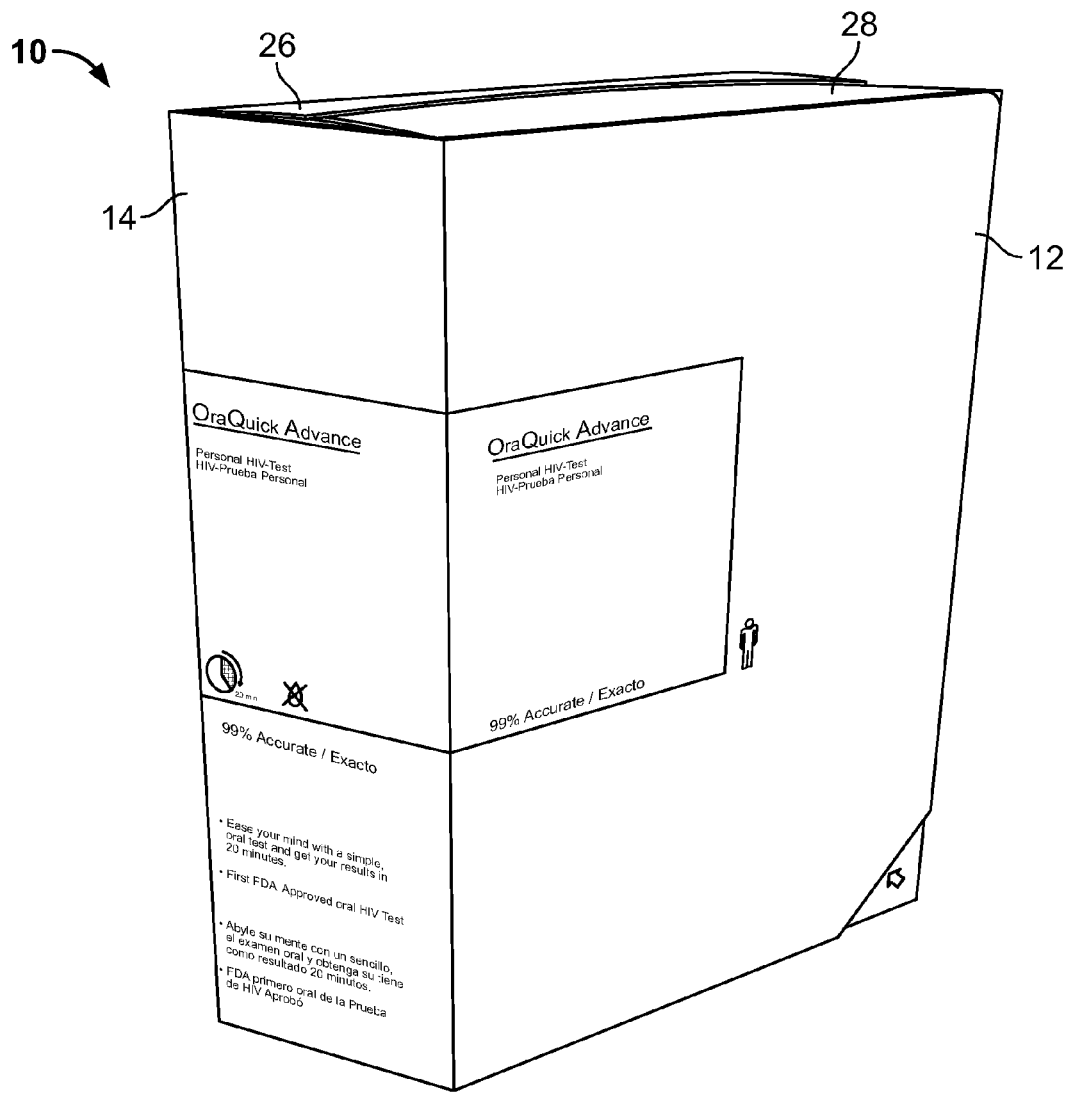
FIG. 2 is a side view of the testing container of FIG. 1.

The present invention relates to a container and method that guides use of devices and/or components employed in home testing systems that diagnose the presence of infectious diseases in an individual. Referring to FIG. 1, a container 10 provides access to the devices and/or components and sequential access to instructions or information relating to the use thereof. Although described and illustrated in relation to the home testing of HIV, it should be appreciated that the testing of other infectious diseases, or testing for the presence of one or more predetermined biological markers, proteins, agents, and/or substances, as well as the general methodology of sequential access to devices, articles, and/or instructions relating to the use thereof in a testing system is contemplated by the present concepts.

The container 10 may be formed from cardboard. Alternatively, the container 10 may be formed from foam or injection-molded from a material, such as polypropylene, polypropylene copolymer, high density polyethylene, or any other appropriate material. It should be appreciated that materials capable of sterilization may be employed with the embodiments described herein. As will be described further below, the container 10 may have a plurality of compartments, recesses, or similar structures for receiving or storing the devices or components of the testing system. In general, the container 10 can be adapted in size and shape to accommodate the devices or components to be contained therein. For example, the container 10 can be a square, rectangle, oval, or circle.

Figure 3:
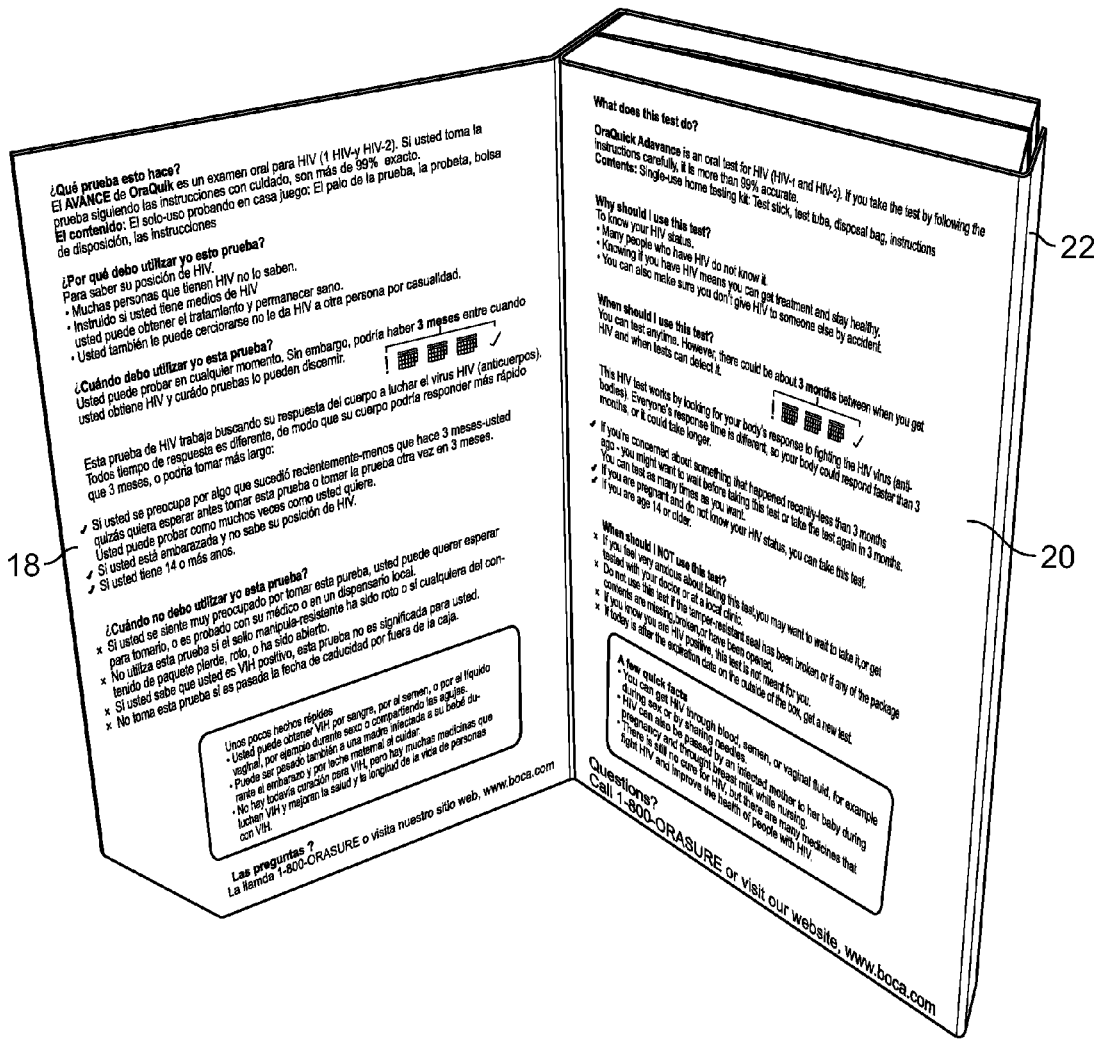
FIG. 3 is a perspective view of the inside cover of the container of FIG. 1.
Figure 4:
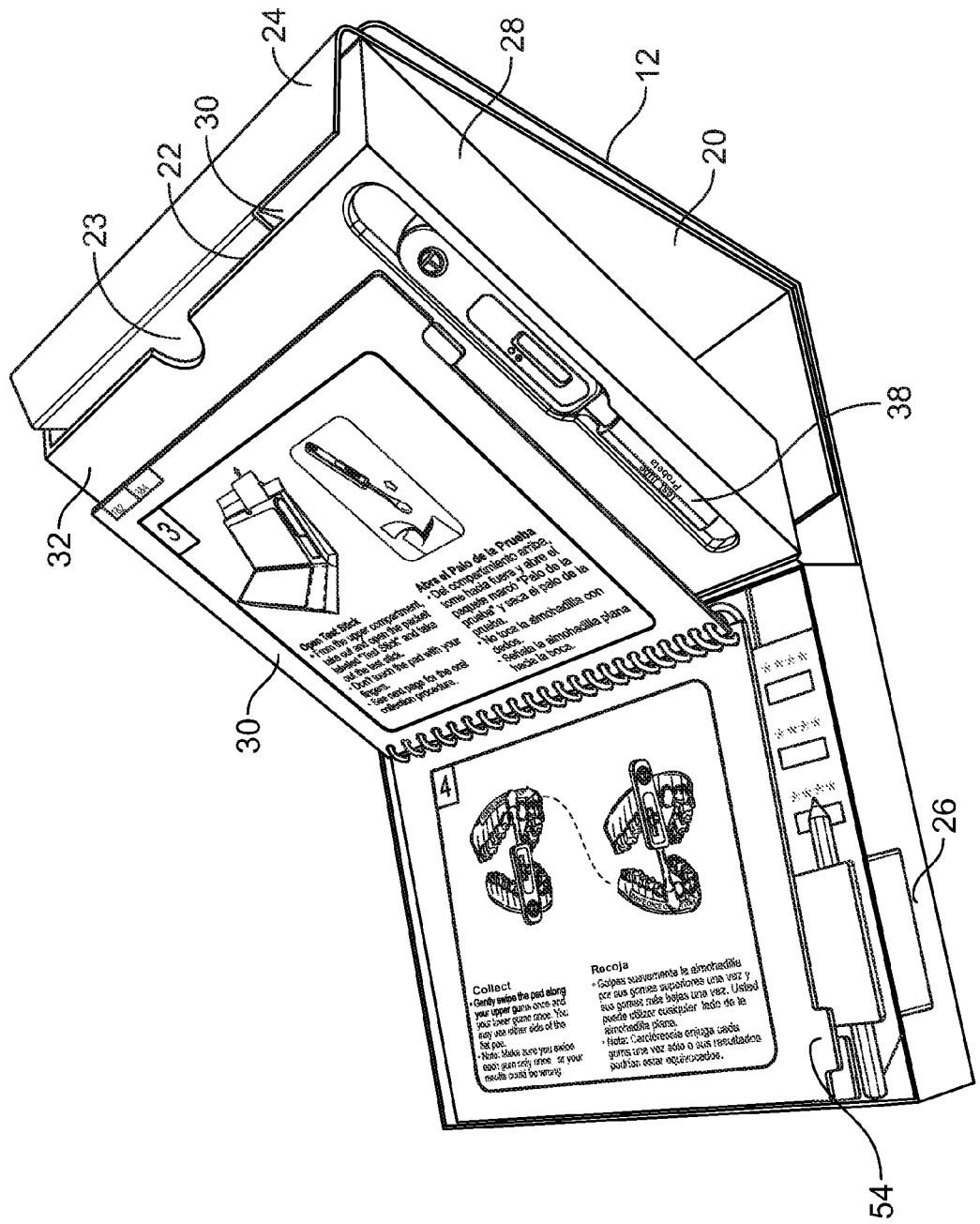
FIG. 4 is a side view of the interior of the container of FIG. 1

As shown in FIG. 1, the container 10 has a front cover 12. The front cover 12 includes a binding 14 and an interior 18. A back 16 shown in FIG. 6 of the container 10 is attached to an inner cover 20 as shown in FIGS. 3 and 4. The front cover 12, the binding 14, the inside 18 of the front cover, the back 16, and the inner cover 20 include written indicia thereon. The written indicia, which can be printed directly thereon or can be a sheet of paper or card stock, plastic or other material laminated or adhered thereto, can include identifying information, preliminary instructions, warnings, and the usage of the device, product or article housed in container 10. As an example, instructions relating to the OraQuick® ADVANCE Rapid HIV-1/2 Antibody Test are illustrated in the various Figures. However, information relating to other diagnostic tests or use of the specific products contained in the container can be printed on these surfaces.

Figure 5:
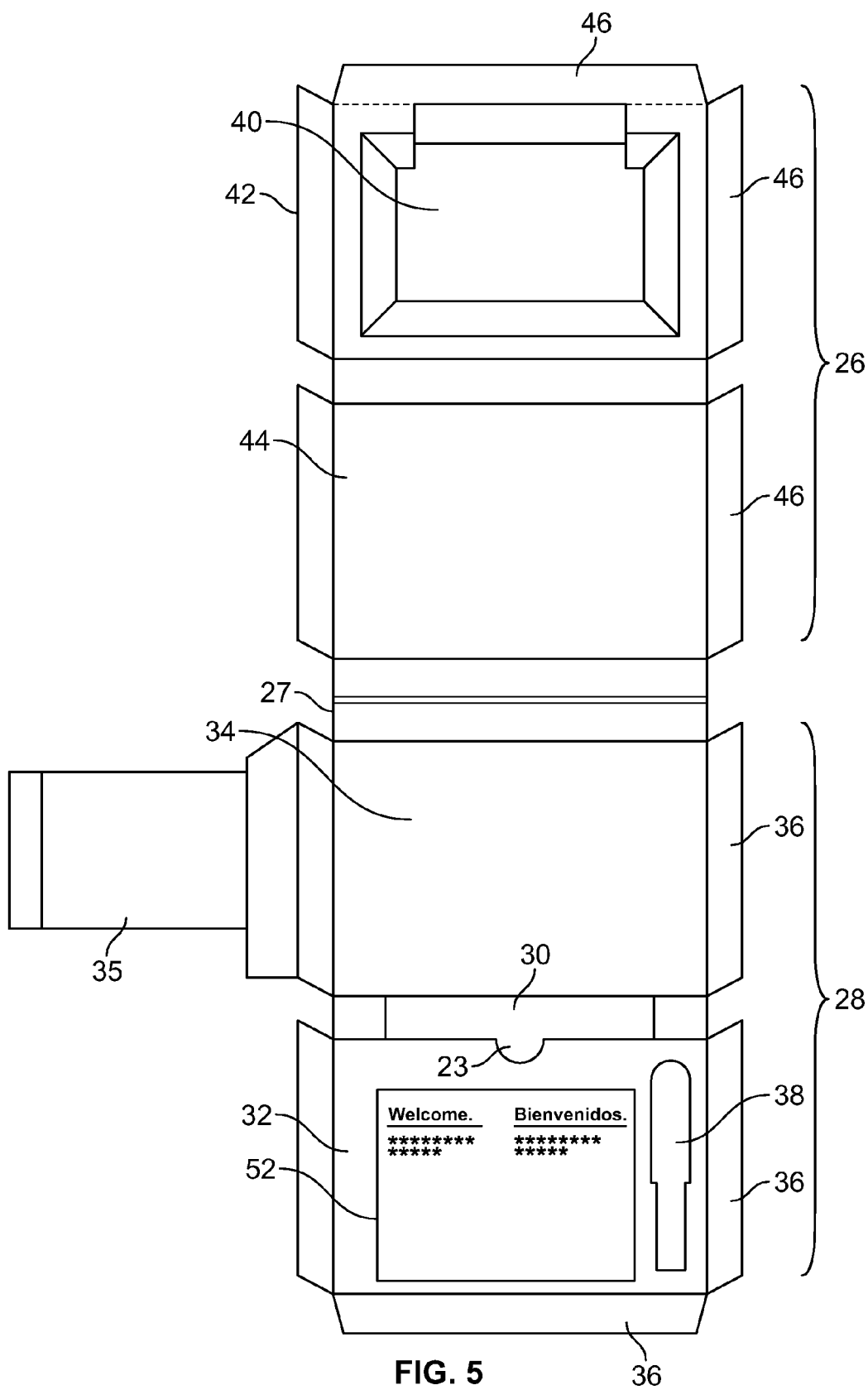
FIG. 5 is a view of the interior of the container of the present invention in a non-assembled state.

Referring to FIGS. 4 and 5, the container 10 has a lower portion 26 and an upper portion 28. The upper portion 28 forms at least one cavity 30 therein. The upper portion 28 includes a top surface 32, a bottom surface 34, and sides 36. When assembled, the surfaces and sides form the cavity 30. The cavity 30 may be a single void or be subdivided into a plurality of compartments.

Figure 6:
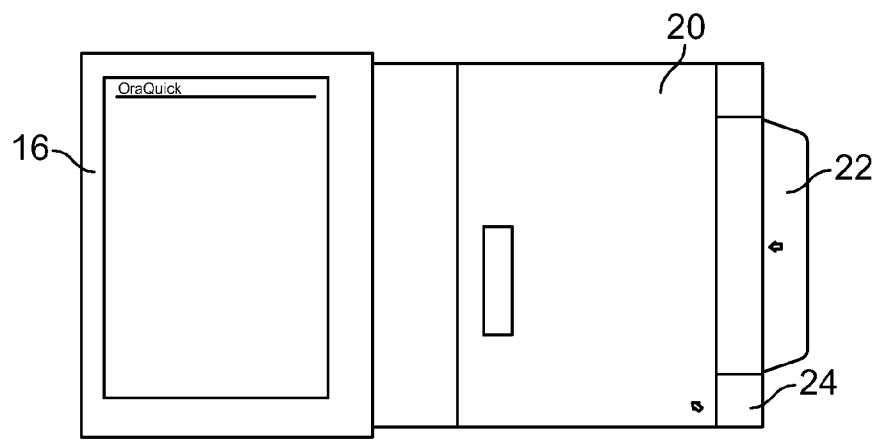
FIG. 6 is a top view of the back and interior page of the container in a non-assembled state.
Figure 7:
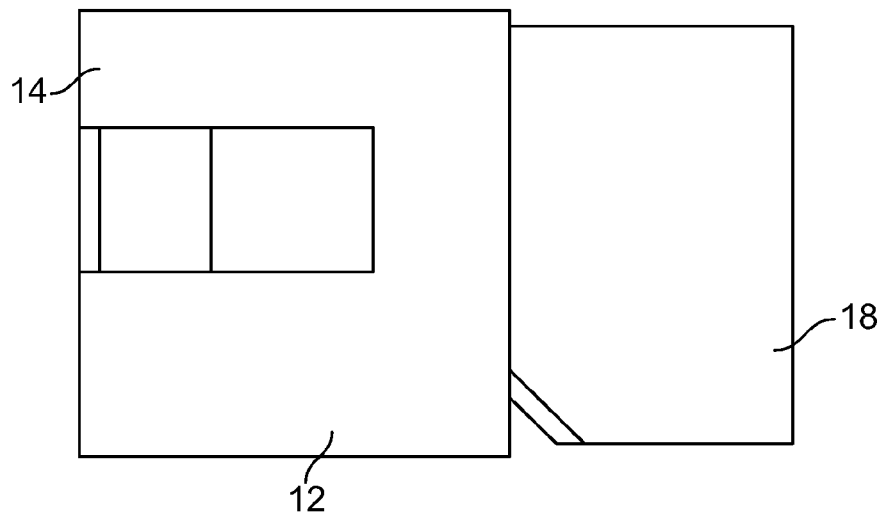
FIG. 7 is a top view of the front cover and inside thereof of the container in a non-assembled state.

When the container 10 is assembled, a flap 22, as shown in FIG. 6, of the inner cover 20 covers access to the cavity 30. As will be explained further herein, the user will encounter written instructions prior to being prompted to remove the devices or articles enclosed in the cavity 30. The flap 22 is sized so as to completely cover access to the cavity 30. The flap 22 can be friction fit within the cavity. However, it may be removably attached to the top surface 32 of the upper portion 26 shown in FIG. 5, for example, via an adhesive, so as to provide a seal therebetween. Alternatively, a projection or flange can be located at spaced intervals or along the entire length on the top surface 32 to hold the flap over the cavity 30. Other types of retention features are contemplated by the present invention. Ultimately, the retention feature keeps all the devices/articles located within the cavity 30 in the container 10, preventing the user from easily turning the container 10 over and removing all inserts at once.

When removal of the flap 22 is desired a finger-hole 23 is provided to enable the user to lift or remove the flap 22 from the top surface 32. The finger-hole 23 can be a slot, cut out at the edge of the top surface, a pull-up, or any other mechanically equivalent device. Furthermore, the flap 22 or edge 24 shown in FIGS. 4 and 6 can be permanently sealed about its edges to the top surface 32, or a respective lip or wall of the upper portion. To remove the device or article from the cavity 30, perforations can be provided about the circumference of the edges such that the flap 22 or edge 24 can be torn and removed therefrom. A release strip having a pull-tab can also be provided for ease of removal. In another embodiment, a separate film is located above and/or below the access to the cavity 30, wherein upon removal of the film, the user could then remove the device or articles.

As will be discussed further herein, the upper portion 28 also includes a space 38 to receive the devices or components of the testing system after they have been removed from the cavity 30 or other compartments. As shown in FIG. 4, for example, a space 38 can receive the OraQuick test vial and flat pad after the test has been preformed. An extension 35 is provided on one side of bottom surface 34.

As shown in an unassembled state in FIG. 5, the upper and lower portions 26, 28 can be connected together via a connecting portion 27. The lower portion 26 includes a top section 42, a bottom section 44, and sides 46.

Figure 8:
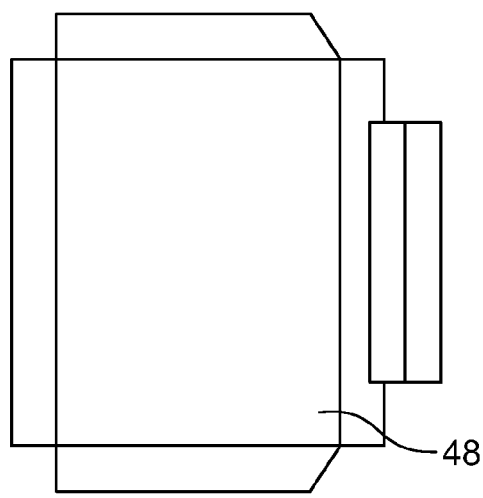
FIG. 8 is a top view of a bottom page of the container in a non-assembled state.
Figure 16:
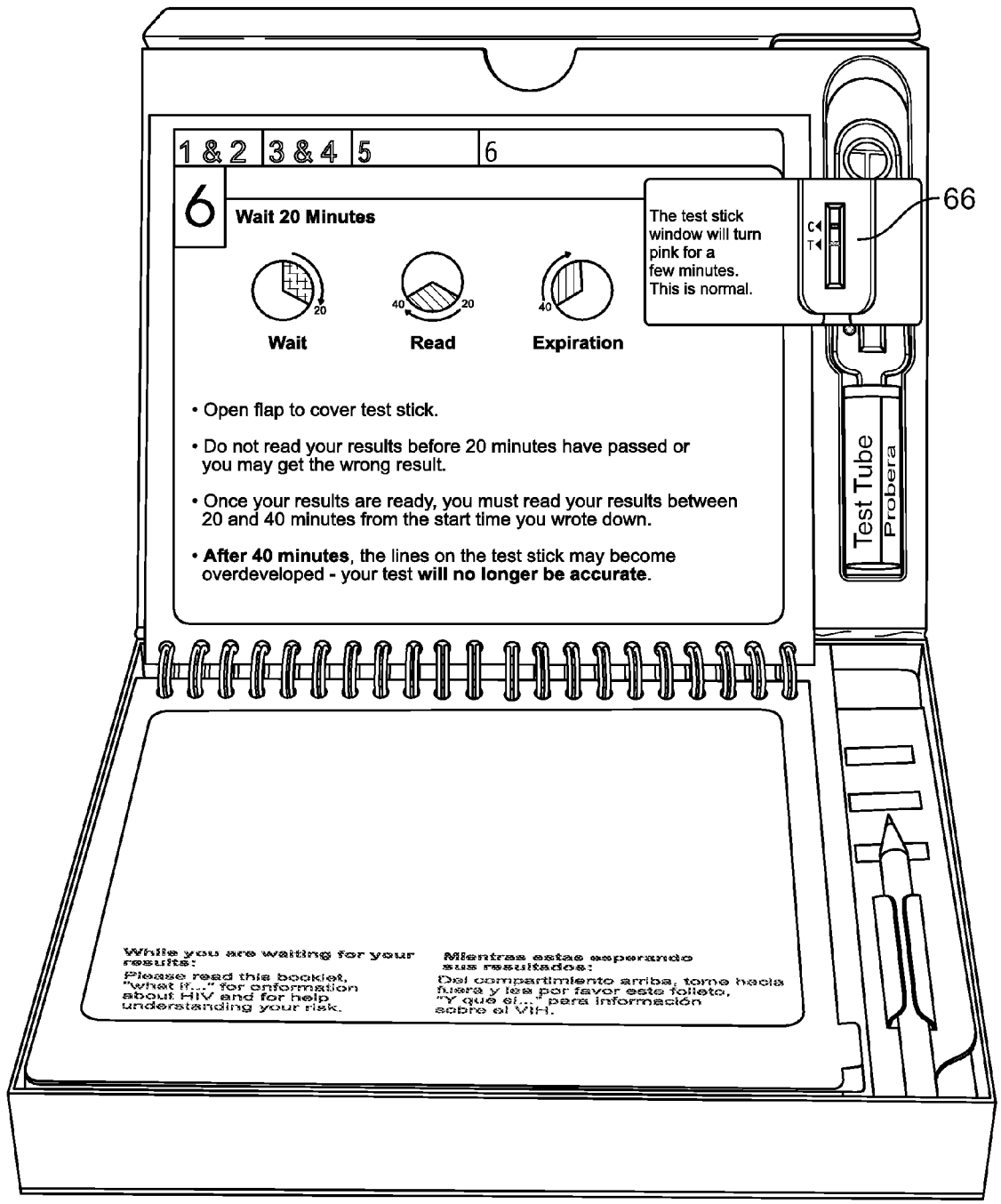
FIG. 16 illustrates sequential written instructions and access to information in the container.

As shown in FIG. 4, the lower portion 26, in some embodiments, also forms a recess, or a well, 40 in the top section 42. The recess 40 can be a single void or be subdivided into a plurality of compartments. A sheet 48, as shown in FIGS. 8 and 16, can extend over the recess 40. An aperture can be located between the sheet 48 and the top section 42 for the user to access devices, articles, pamphlets or other components stored in the recess 40. The sheet 48 can be made of cardboard, foam, or an injection molded material, such as polypropylene, polypropylene copolymer, high density polyethylene, or any other appropriate material. It should be appreciated that the sheet 48 is formed from a sufficiently strong material so that the sheet 48 will not collapse into the recess 40. Moreover, the sheet 48 can also include indicia and/or spacing whereby a user can record test results thereon. The sheet 48 can be removably attached to top section 42, for example, via an adhesive, so as to provide a seal therebetween. Alternatively, a projection or flange can be located at spaced intervals or along the entire length of the sheet 48 to locate it over recess 40. Other types of retention features are contemplated by the present invention. Ultimately, the retention features keeps all the devices/articles located within the recess 40 in the container 10.

Referring again to FIG. 4, a removable instruction insert 50, such as a flip chart, can be located in the container, for example, between the upper portion 26 and lower portion 28. Although described as a single insert, the present invention contemplates a plurality of inserts located within the container. Flip chart 50 provides a sequence of instructions, or directions, that guide the user through the test. The inserts can have any shape that would fit within a respective container shape and cover a designated recess and be held therein. However, the inserts need not be of the same shape as the container.

The instruction insert 50 may be a sheet of paper or card stock, plastic or other laminated material, or a pamphlet/booklet. The insert 50 may include advertising information and/or preliminary instructions and warnings regarding the use of the devices and components packaged in the container 10. The insert 50 can include a flip tab 54 on each page as shown in FIG. 4 to help the user turn the pages. The instruction insert 50 may be removably attached to either the upper portion 26 or the lower portion 28, for example, via an adhesive. The instruction insert 50 may be attached to the bottom section 44 or the sheet 48 of lower portion 26 such that it blocks access to the recess 40. A seal can be provided therebetween.

Figure 9:
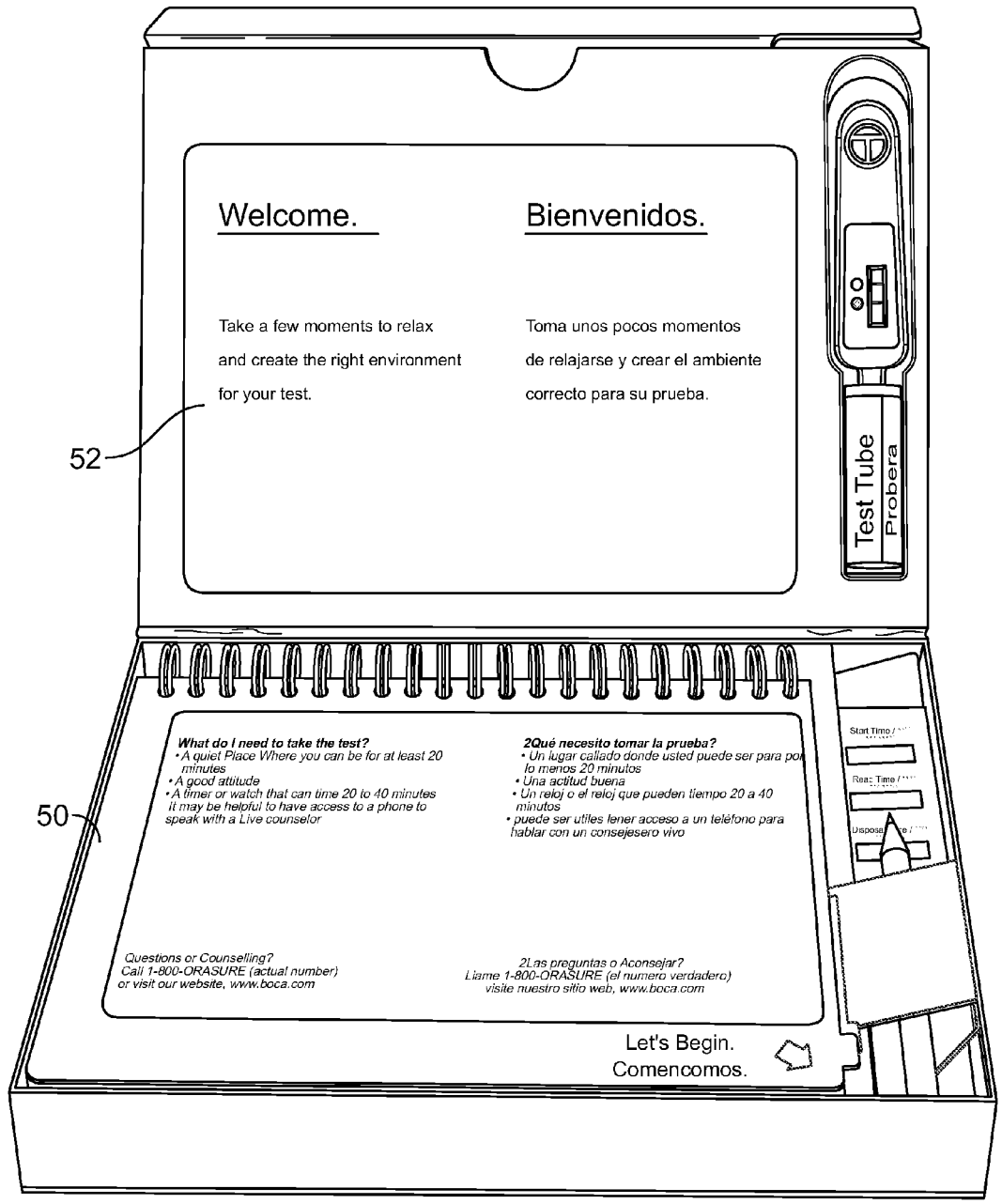
FIG. 9 is a perspective view of the interior of the upper portion of the container of FIG. 1.

Referring to FIGS. 9-21, a particular embodiment of a package, for example an OTC home HIV test, such as a version of the OraQuick® Rapid HIV-1 Antibody Test, is shown. As shown in FIG. 9, the insert 50 may be a spiral-bound booklet having a sequence of instructions for using the test. The top surface 32 provides a welcome message or introduction for the user. The insert 50 is located between the upper and lower portions such that as the pages are flipped up the welcome screen is covered, as is the preceding top page.

Figure 10:
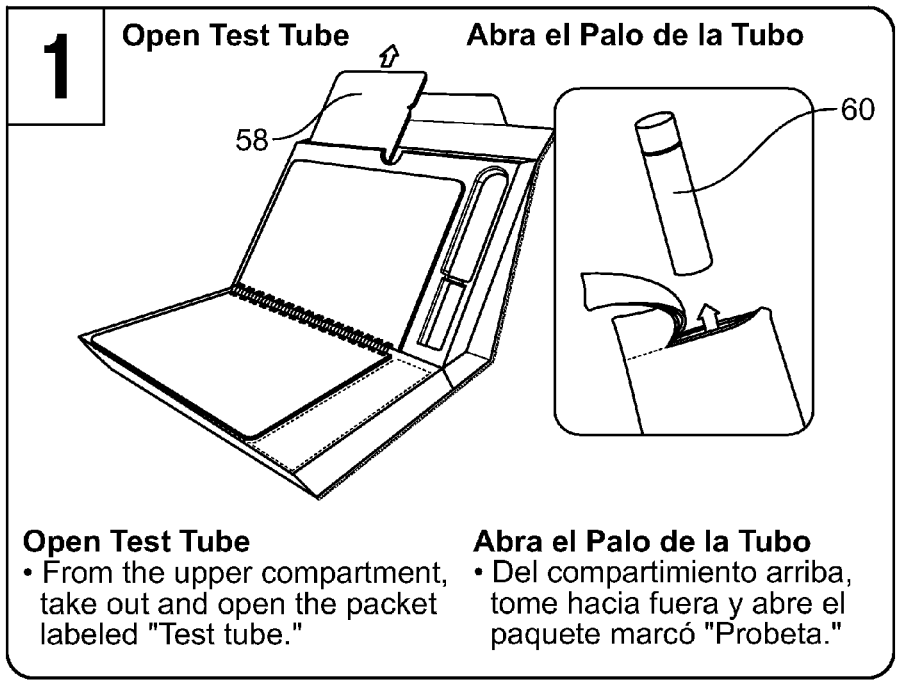
FIG. 10 illustrates a first step in the directions for the sequential access to the testing product.
Figure 11:
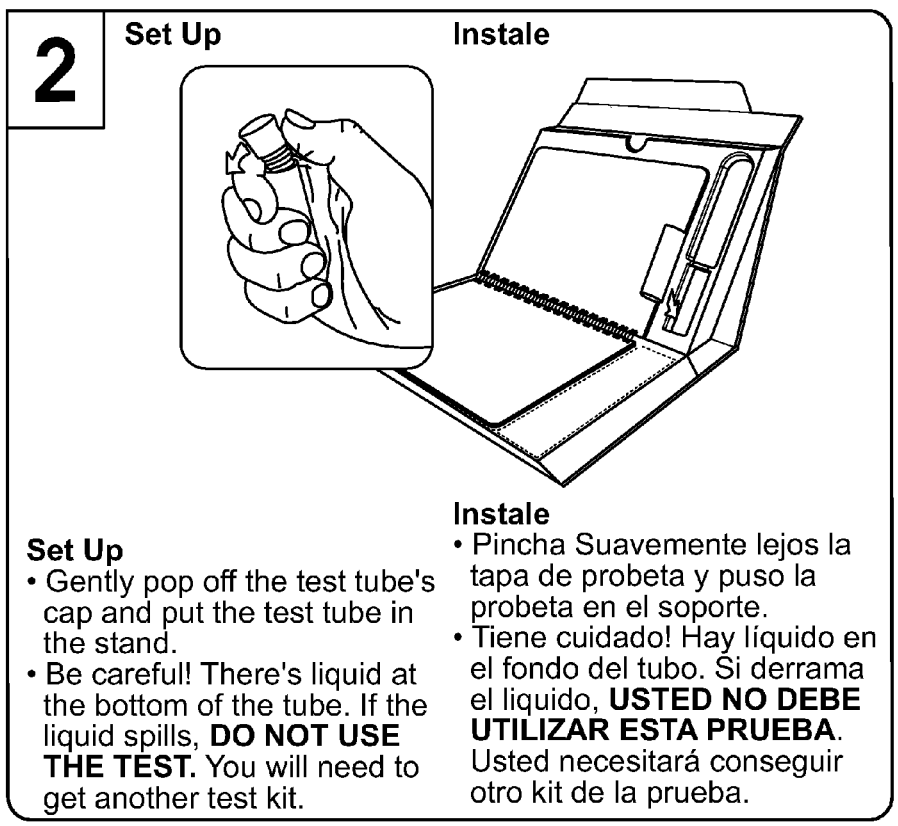
FIG. 11 illustrates a second step in the directions for the sequential access to the testing product.

As discussed previously, the cavity 30 can include a plurality of devices or components. Referring to FIG. 10, the first page of insert 50 instructs the user on how to access the devices or components of the testing device. A sealed package 58 can be located in the cavity 30. The user is instructed to open the cavity 30 in the upper portion 28 and remove the package 58. The package 58 may provide a vial or test tube 60. As shown in FIG. 11, page 2 of the insert instructs the user to remove the cap of the vial 60 and place the vial 60 in the space 38 of the lower portion 28. Instructions regarding the removal, purpose, and operation of the vial 60 may be provided by the insert 50 before the user access the package 58. It should be appreciated that the multiplicity and complexity of components may require unique and specialized instructions.

Figure 12:
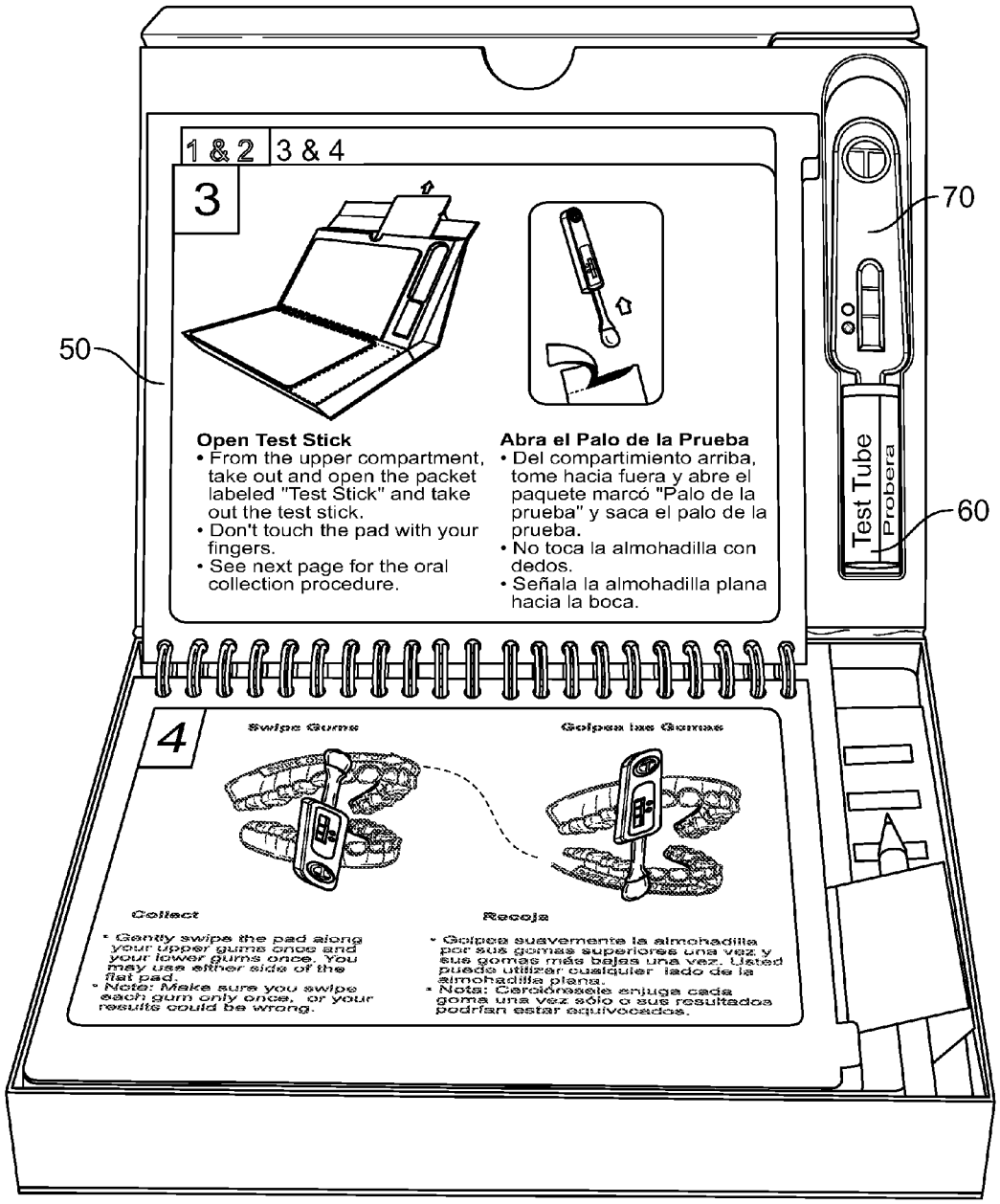
FIG. 12 is a perspective view of the inside container during the third and fourth steps.
Figure 13:
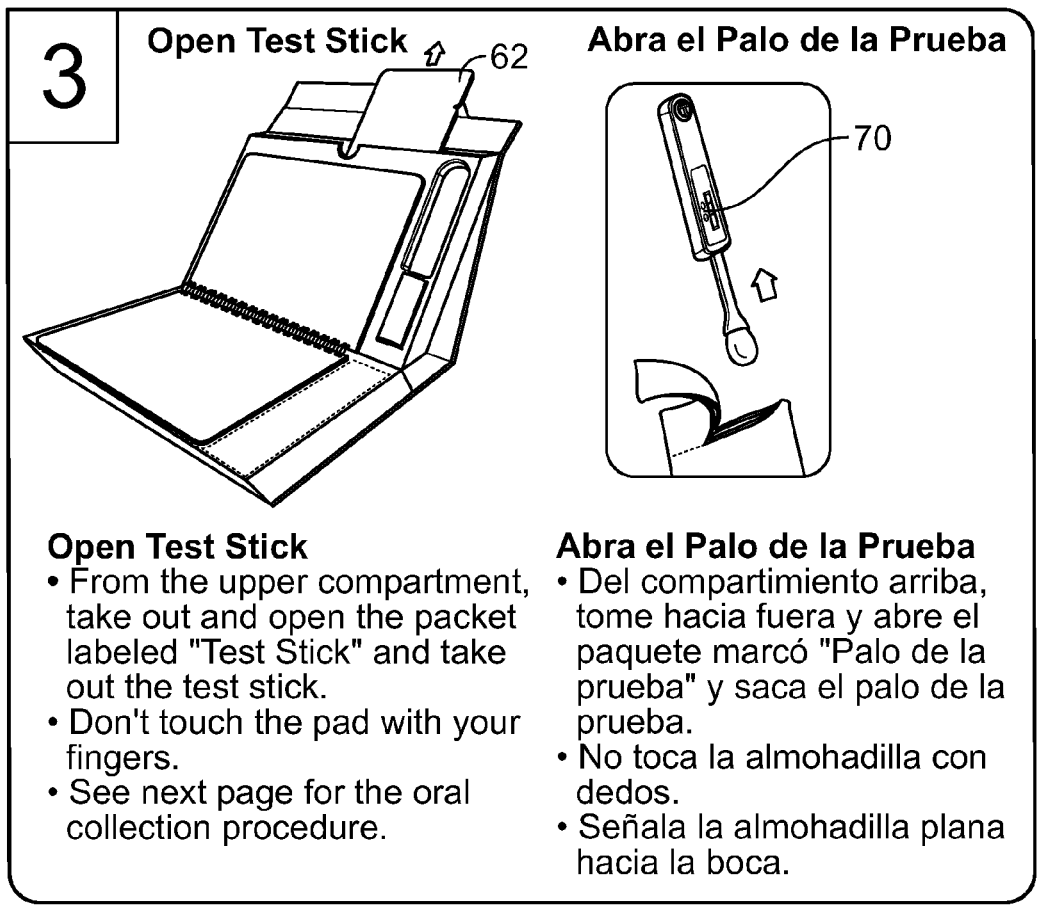
FIG. 13 illustrates the third step in the directions for the sequential access to the testing product and the directions for use.
Figure 14:
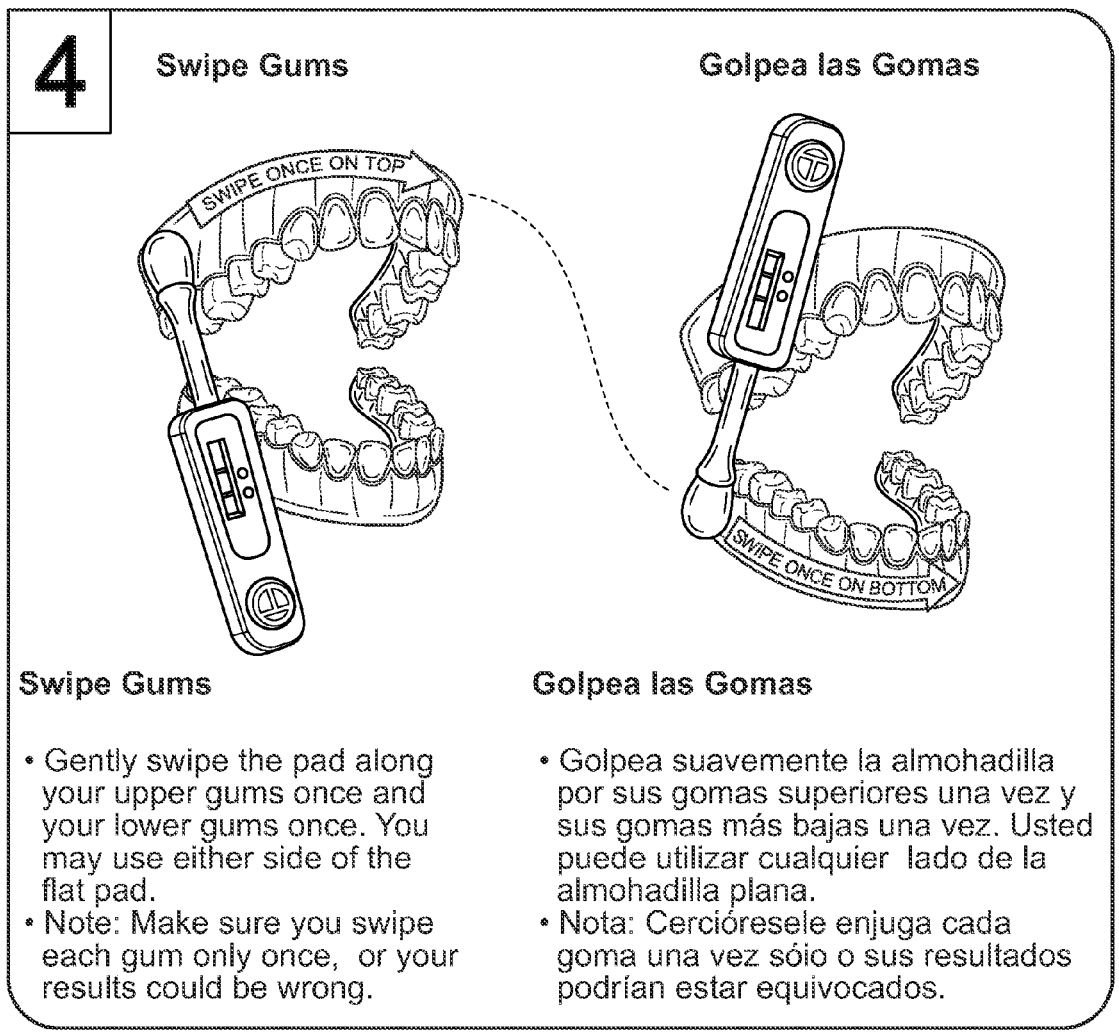
FIG. 14 illustrates the fourth step in the directions for use.

As shown in FIGS. 12-14, another package 62 can be located within an additional compartment of the cavity 30 or placed side-by-side, or behind, the package 58 within the cavity 30, such that it can be accessed and removed. Once the package 62 is opened, an OraQuick® test stick device 70, for example, can be removed from the package 62. Insert 50 includes instructions on how to use test stick 70 to perform the test. As shown in FIG. 15, the user is then instructed to place device 70 in vial 60.

Figure 17:
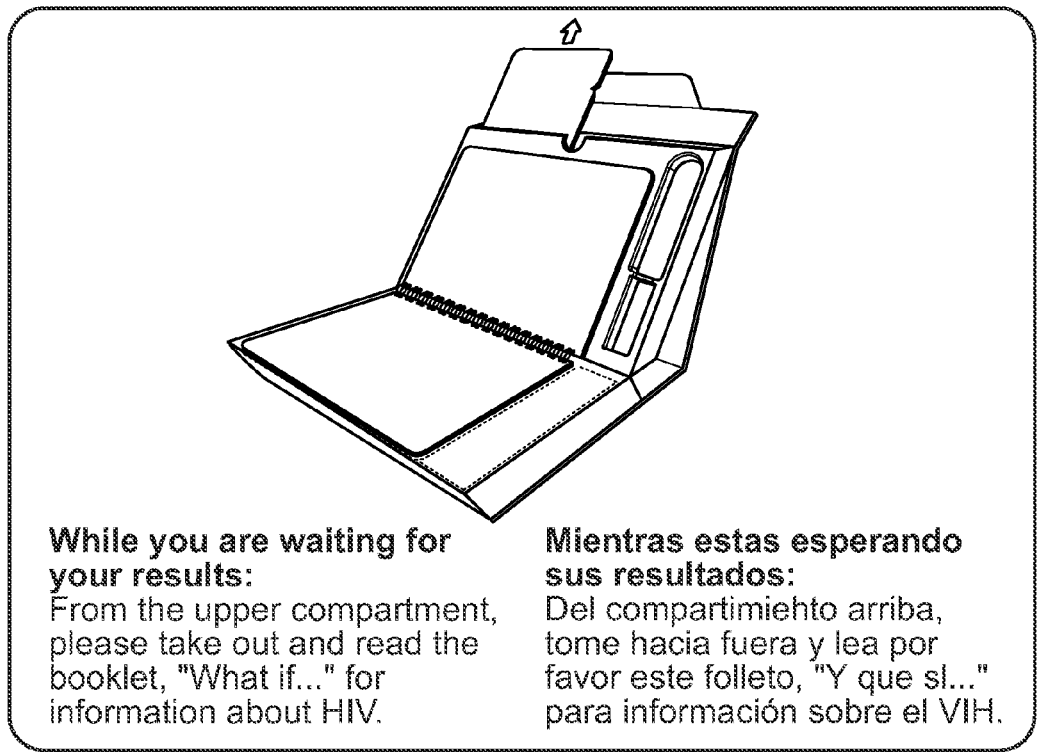
FIG. 17 illustrates the next step in the sequential written instructions.

Thereafter, the user is instructed, as illustrated in FIGS. 16-17, to wait for the test results. During that time the user is prompted to remove booklet 90 shown in FIG. 18A that is stored within recess 40 and read the information therein.

The next step in the sequence is illustrated in FIG. 19. The sheets of insert 50 for steps 6 and 7 include a tab 66 that covers the actual test stick 70 while the device is processing the test. In sheet 7, the user is prompted to remove tab 66 to view the test results and to determine if the result is negative, i.e., the HIV-1 and HIV-2 antibodies were not detected in the specimen, or positive, i.e., the HIV-1 and HIV-2 antibodies were detected in the specimen.

Figure 18A:
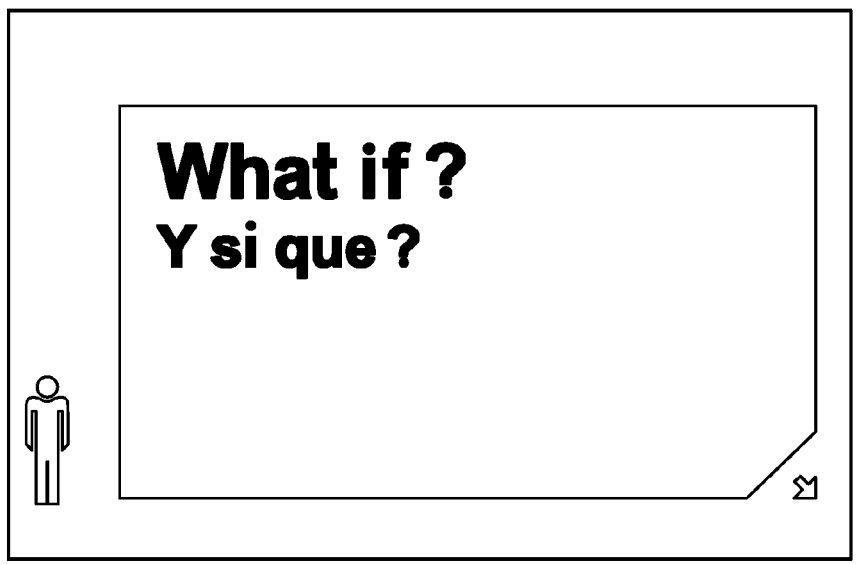
FIGS. 18A-18C illustrate top views of the informational booklets located in the container.
Figure 18C:
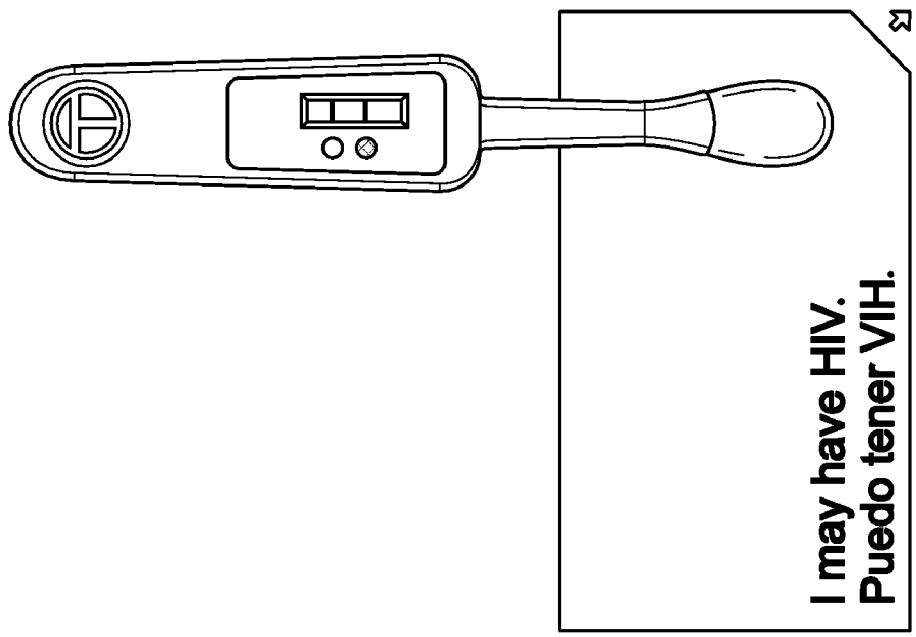
Figure 18B:
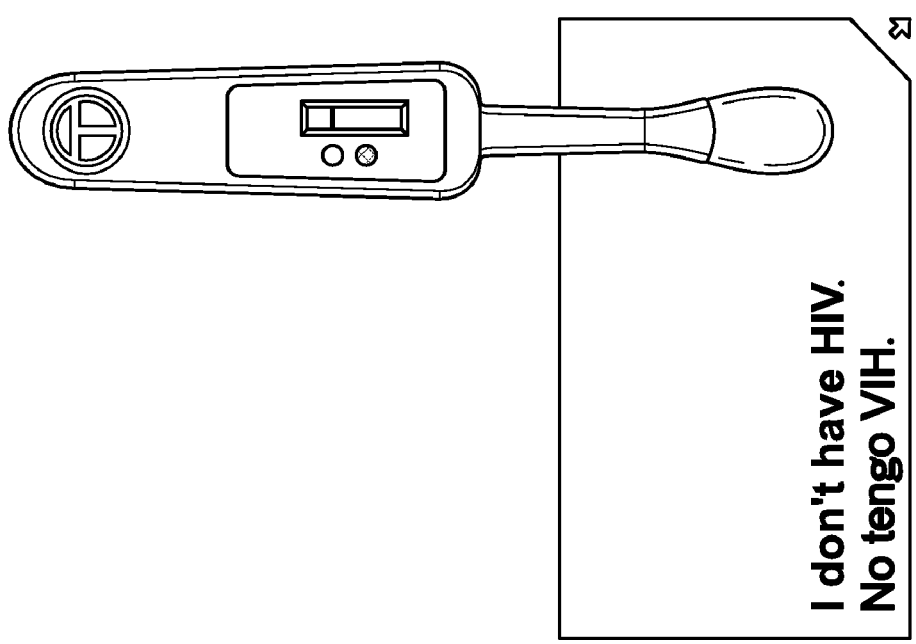
Figure 20:
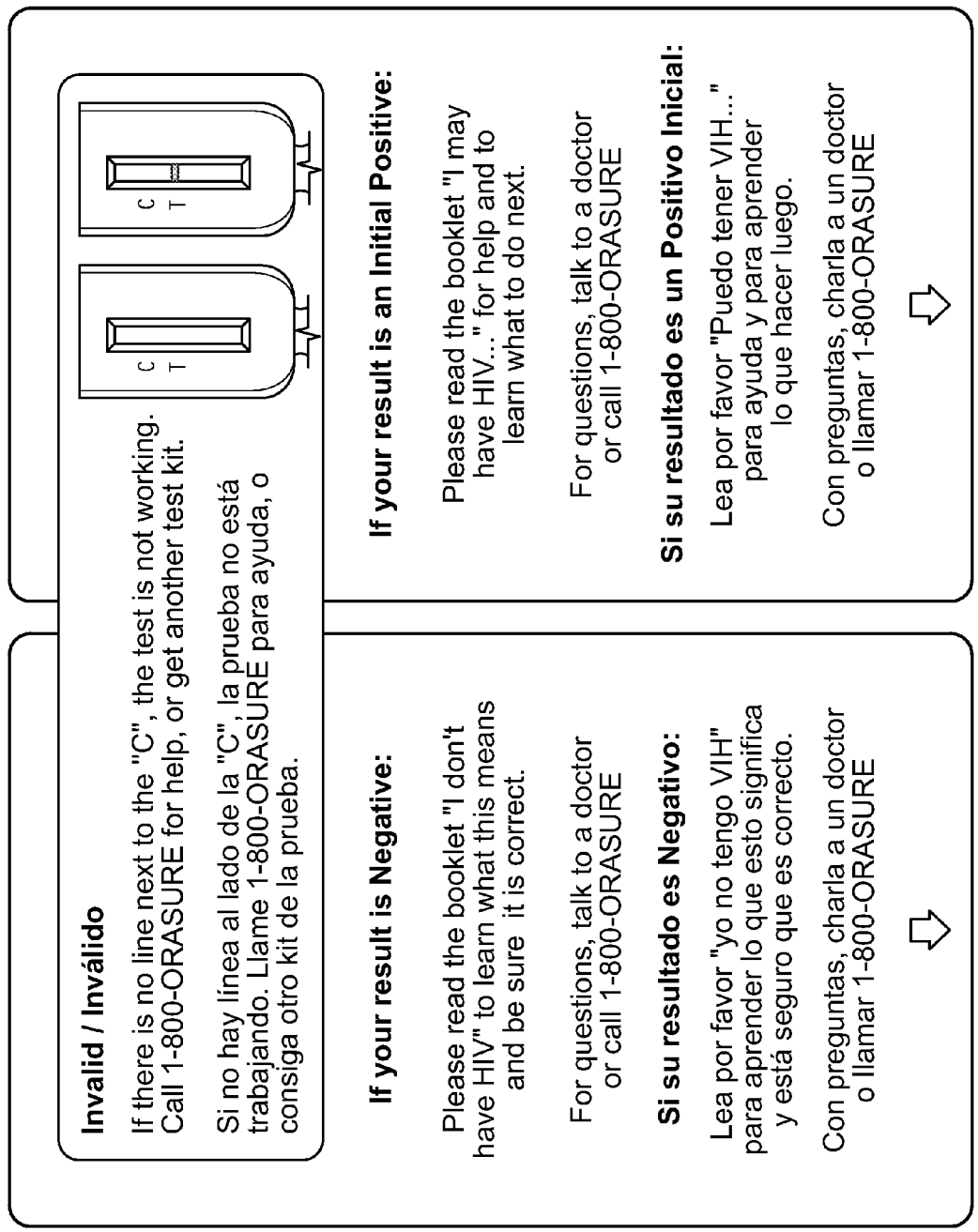
FIG. 20 illustrates the sequential instructions for completing the test.
Figure 21:
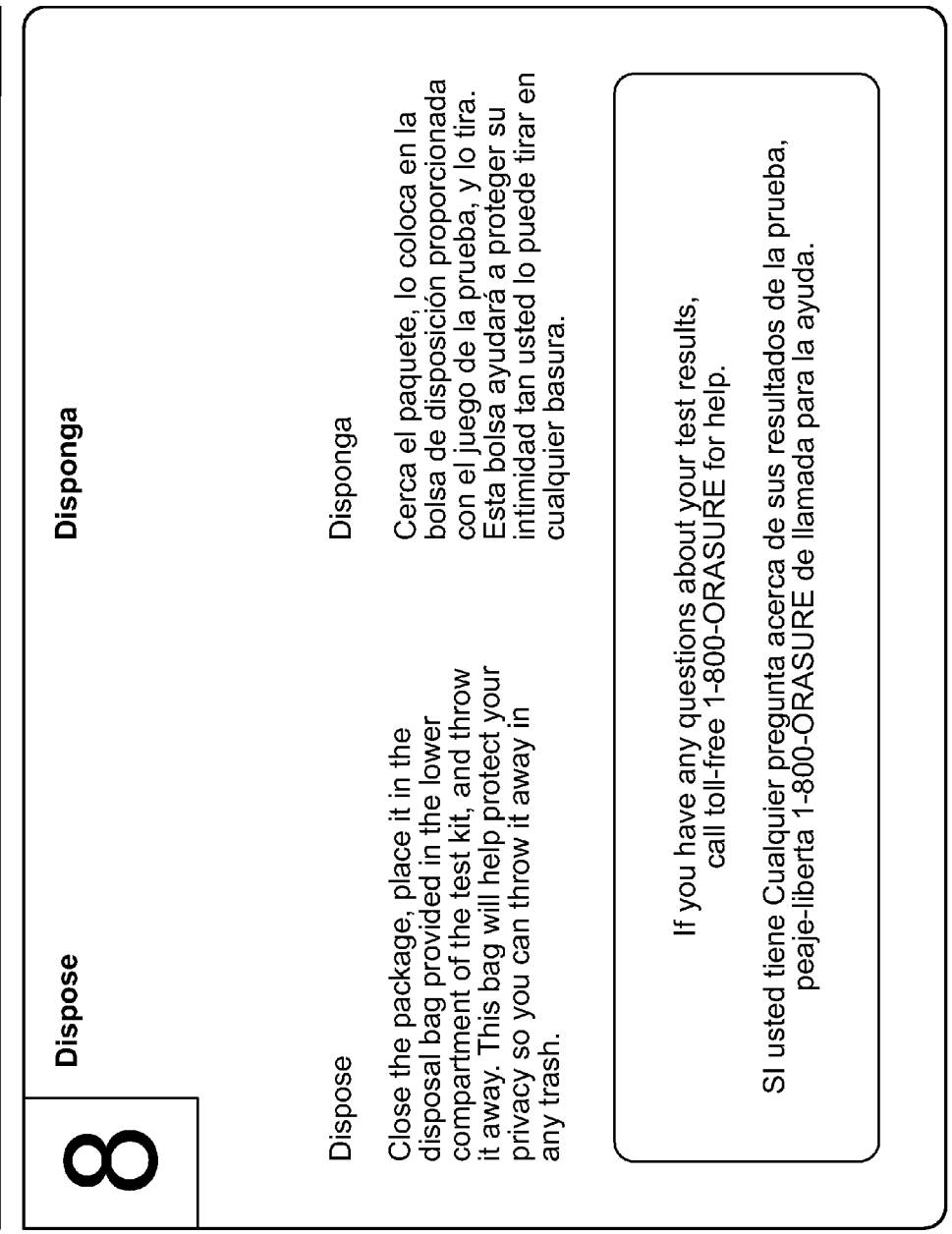
FIG. 21 illustrates the sequential instructions for disposing of the test upon completion.

As shown in FIG. 20, depending on the test result, the user is prompted to remove the corresponding pamphlet shown in FIGS. 18B and 18C from the recess 40. Thereafter, the insert 50 provides instructions for the user to dispose of the container as shown in FIG. 21.

Although, the interior of the container 10 of the present device has been described with reference to a particular embodiment, as discussed previously, numerous combinations and types of devices and components can be packaged according to aspects of the present invention. Thus, the method of packaging of the present invention is not limited to a particular end use.

It should be appreciated that not all instruction inserts need to be sealed in the container. For example, an insert could be a parts list. Moreover, in another embodiment, one well or cavity may be covered with an insert whereby removal thereof would allow the user to access a key or other mechanism, which in turn would be required to open a sequential insert or cavity.

In operation, the method of packaging to allow sequential access to articles contained therein includes positioning article(s) within all or some of the cavities of the tray. Thereafter, all or some of the cavities can be covered and/or sealed with an insert. As discussed previously, if a particular article has specific instructions or warnings, an insert specific thereto may be used to cover the cavity in which the particular article is stored. The remaining cavities and insert can then be covered with a subsequent removable insert that covers or seals the subsequent recess located above the cavities. This sequence is repeated as necessary until all the necessary instructions or warnings have been positioned. The upper recess is then sealed or covered with the first insert. During dispensing, the upper insert must first be removed, sequentially followed by any subsequent inserts before the article(s) can be retrieved from the cavities. In other words, the number of inserts or covers, are adapted to accommodate the specific testing system provided with the container 10. In some embodiments, the container can have any number of recesses or wells where each is covered by a respective insert or layers of inserts. Thus, each of the required inserts is disposed in a respective recess, the recess being disposed one beneath another such that the inserts are spaced from one another. The lower inserts can be accessed only after the preceding insert is removed. In such embodiments, the container increases user compliance by providing sequential access to the articles or goods packaged therein.

Figure 22:
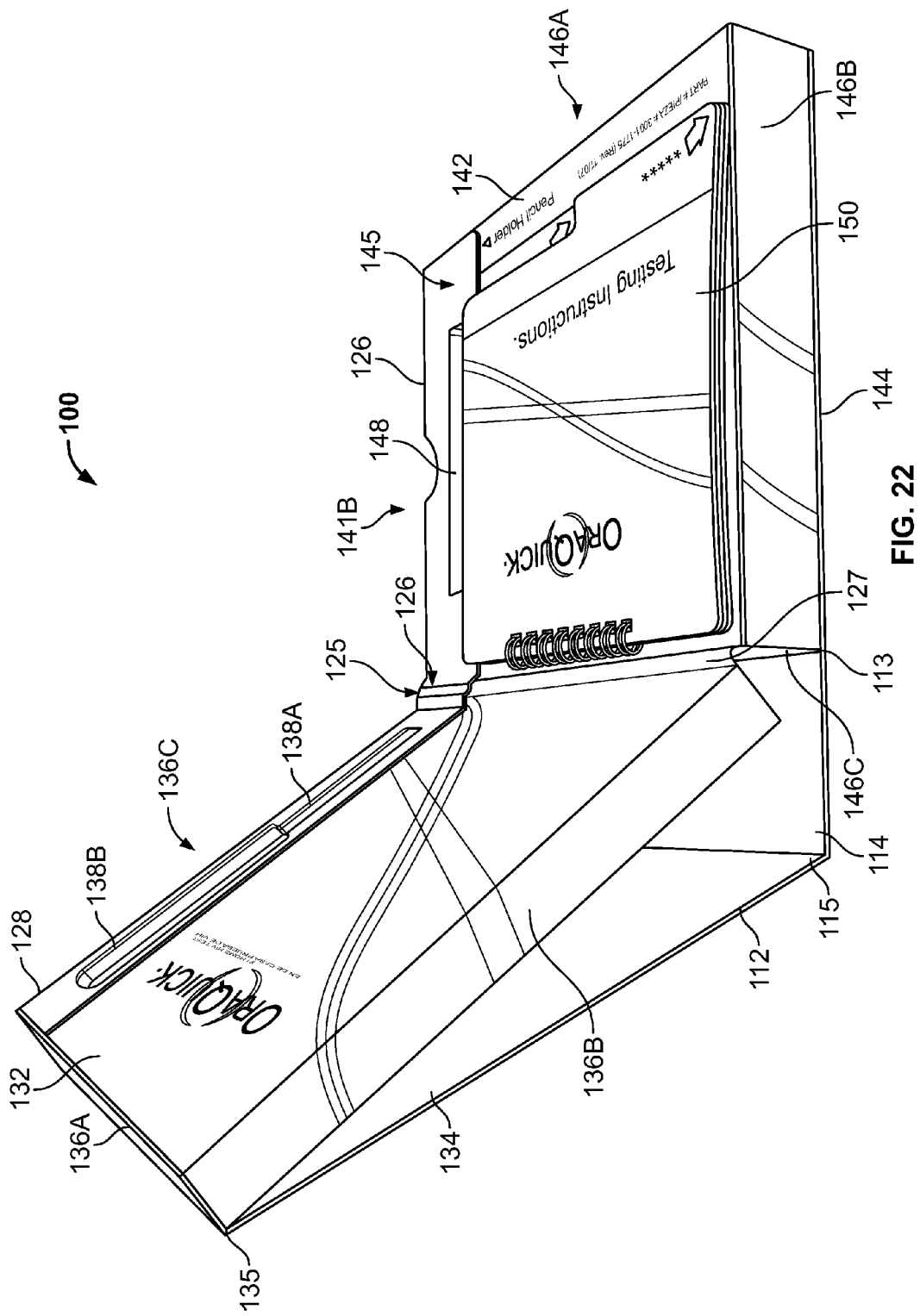
FIG. 22 illustrates a perspective view of another embodiment of a testing container according to aspects of the present invention.

Referring to FIG. 22, another embodiment of a container 100 according to aspects of the present invention is illustrated. As with the container 10 described previously, the container 100 provides access to devices for a testing procedure along with instructions and information relating to the use of the testing devices. The container 100, or portions thereof, may be formed from cardboard, foam, or injection-molded materials, such as polypropylene, polypropylene copolymer, high density polyethylene, or any other appropriate material. It should be appreciated that a material capable of sterilization is also contemplated.

As shown in FIG. 22, the container 100 includes a base 126 and an upper section 128. The base 126 includes an interior surface 142, an exterior surface 144, and side surfaces 146A, 146B, and 146C. Meanwhile, the upper section 128 has an interior surface 132, an exterior surface 134, and side surfaces 136A, 136B, and 136C. The base 126 is, in the embodiment shown, dimensioned to be larger than the upper section 128. This configuration facilitates placement of a tray 140, described below, therewithin, such tray bearing, for example, testing devices. This configuration provides other attendant benefits including enhanced stability of the container 100 during the testing procedure. In addition, the disparity in size between the larger base 126 and smaller upper section 128 provides a visual clue to the user as to indicates how the container 100 should be oriented, i.e., which end should face up, when opened.

A connecting portion 127 connects an edge of the interior surface 142 of the base 126 to an edge of the interior surface 132 of the upper portion 128, so that the upper portion 128 can pivot relative to the base 126 at a hinge 125 defined by the connecting portion 127. In other words, the container 100 can transition in a book-like manner from the closed configuration shown in FIG. 32 to the open configuration shown in FIG. 22. When the container 100 is in the closed configuration, the interior surfaces 132 and 142 are oriented so that they are not visible to the user. When the container 100 is in the open configuration, the interior surfaces 132 and 142 are visible to the user.

Figure 32:
FIG. 32 illustrates a perspective view of the testing container of FIG. 22 in a closed configuration.

A spine 114 connects an edge of the exterior surface 144 of the base 126 to an edge of the exterior surface 134 of the upper section 128. As shown in FIG. 32, the spine 114 separates the corresponding edges of the exterior surfaces 134 and 144 by a distance that is approximately equal to the combined height $H_1$ and $H_2$ of the side surfaces 136 and 146 of the base 126 and the upper section 128, respectively. In this way, the spine 114 is dimensioned to enable the container 100 to be kept in the closed configuration.

Together, the spine 114 and the exterior surfaces 134 and 144 form an outer cover 112. As illustrated in FIG. 32, product information or other indicia 113 may be printed, or otherwise affixed, to the outer cover 112 and/or spine 114. The outer cover 112 can also be used to improve or enhance aesthetic aspects of the container 100, as well as to provide a desired structural integrity and rigidity to the container. Furthermore, when the container 100 is in the open configuration, the outer cover 112 also enables the upper portion 128 to maintain a stable position relative to the base 126. For example, in FIG. 22, the displayed configuration of the outer cover 112 keeps the interior surface 132 of the upper section 128 at a predetermined angle, e.g., between about 120-140 degrees, relative to the interior surface 142, to maximize visibility of the interior surfaces 132 and 142 for the user and to facilitate use of the container 100. Alternatively, in yet other potential configurations, the permitted movement of the upper section 128 relative to the base 126 may be controlled in whole or in part by other movement-limiting members such, as but not limited to, a hinge member such as the hinge 126 of thermoform 145, or by ribbons, wires, strings or the like of any flexible material adapted to restrain movement of the upper section past a predetermined point.

As illustrated by FIG. 32, when the container 100 is in the closed configuration, the exterior surface 144 of the base 126 is situated on a supporting surface, such as a table top. In addition, the exterior surface 134 of the upper section 128 faces upwardly and is substantially parallel to the exterior surface 144 of the base 126. Meanwhile, the spine 114 is substantially perpendicular to the exterior surfaces 134 and 144. In typical operation, the user handles the upper section 128 to transition the container 100 into the open configuration as shown in FIG. 22. As described above, the upper section 128 pivots at the hinge 125 defined by the connecting portion 127. As the upper section 128 pivots, the spine 114, which is connected to the exterior surface 134 of the upper section 128, correspondingly pivots at a hinge 113 defined by the connection between the spine 114 and the exterior surface 144 of the base 126. To allow the spine 114 to pivot freely at the hinge 113, the spine 114 also pivots at a hinge 115 defined by the connection between the spine 114 and the exterior surface 144. The exterior surface 134 in turn pivots at a hinge 135 defined by a connection between the exterior surface 134 and the side surface 136A. As shown in FIG. 22, the exterior surface 134 is only attached to the upper section 128 at the side surface 136A, and the rest of the exterior surface 134 is permitted to move away from the rest of the upper surface 128. The spine 114 pivots until it lies stably against the supporting surface, as shown in FIG. 22. At this point, the exterior surface 134 extends from the spine 114 to the hinge 135 to vertically support the rest of the upper section 128. Any further pivoting movement by the upper section 128 away from the base 126 is prevented by the resistance of the exterior surface 134 to buckling. Optionally, further pivoting movement by the upper section 128 away from the base 126 may be prevented, in whole or in part, by resistance of the thermoform 145 hinge 126 or by any other movement-limiting member(s) or device(s).

Figure 29:
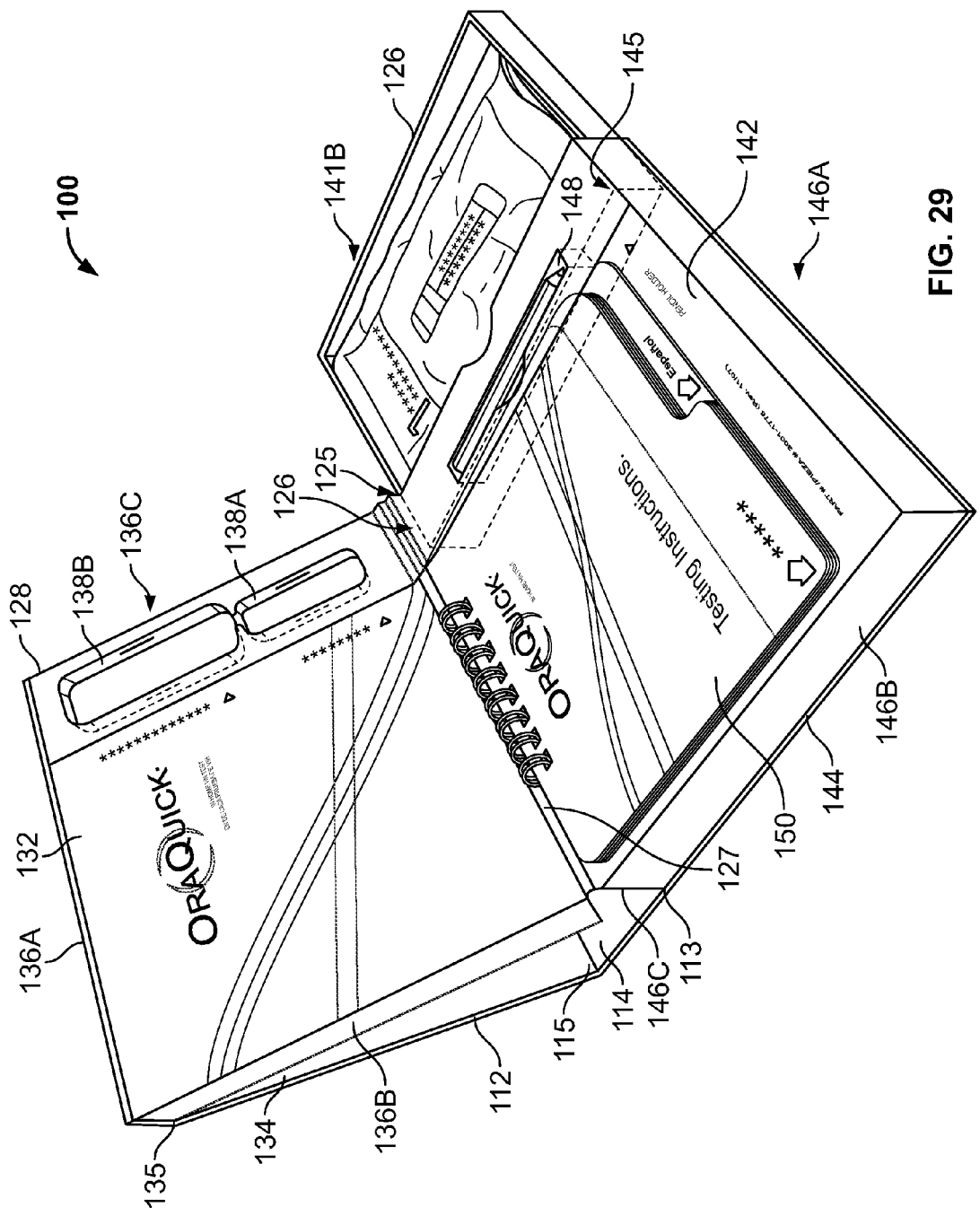
FIG. 29 illustrates a perspective view of the testing container of FIG. 22, showing a tray containing devices and other components of the testing system.

As shown in FIG. 29, the base 126 includes a tray, or drawer-like structure, 140 that slides from a cavity 141A through a side opening 141B. The cavity 141A is defined by the interior surface 142, the exterior surface 144, and side surfaces 146A, 146B, and 146C. As described further below, the tray 140 stores devices, or components, for the testing system until the user is expressly instructed to access and handle them. Informational and/or instructional packets, papers, or brochures may also advantageously be provided therein. The testing devices are organized in the tray 140 according to the sequence in which they should be accessed. For example, packets containing testing devices that should be accessed earlier in the testing procedure may be more easily retrieved from the tray 140.

The base 126 may also include at least one recess 148 at the interior surface 142 to hold a device or component that is used during the testing procedure. In the illustrated embodiments shown in FIGS. 22-32, the recess 148 is defined by a thermoform member 145. In one embodiment, the recess 148 holds a pencil 149 to make it more convenient for the user to note important information. The recess 148 may advantageously extend through the interior surface 142 into the cavity 141A to form a stop that engages a distal tray wall and prevents the tray 140 from being pulled completely out of the cavity 141A. In this way, it is less likely that the testing devices in the tray 140 will fall out of the tray and become disorganized or contaminated.

Meanwhile, referring again to FIG. 22, the interior surface 132 of the upper section 128 includes recesses 138A and 138B formed in a plastic thermoform member 145 to hold testing devices during the procedure, as described further below. The recesses 148, 138A, and 138B may be defined by a plastic thermoform 145, as shown, or may be formed directly into the material forming the base 126 and/or upper section 128. The thermoform 145 for recess 148 is fixed to the interior surface 142, while the thermoform for recesses 138A and 138B are fixed to the interior service 132. The thermoform(s) 145 may be fixed by adhesive, fasteners, tight frictional engagement, and/or mechanical interlocking, such as tabs that act to snap the thermoform into place. Moreover, the thermoform(s) 145 may be shaped to correspond closely with the device or component. In some embodiments, the thermoform(s) 145 may be shaped, for example, with detents, to hold the device or component in place. In still other aspects, the depicted thermoform 145 may be provided in separate parts (e.g., a separate part for the upper section 128 and for the base 126).

The interior surface 132 of the upper section 128 may include, but is not limited to, a company name and/or logo, product information or indicia, such as an introductory message and/or preliminary textual and/or graphical instruction(s), provided on or otherwise affixed to the interior surface 132. Meanwhile, a detailed instruction insert 150 for guiding the user during the administration of the test may be provided as, in one aspect, a spiral-bound flip-book are attached to the interior surface 142. As such, the instruction insert 150 is disposed between the interior surface 142 of the base 126 and the interior surface 132 of the upper section 128. If necessary, the interior surface 132 and/or the interior surface 142 may also be recessed to accommodate the instruction insert 150, especially if the instruction insert 150 requires many pages. Advantageously, the instruction insert 150 is readily available to the user during the testing procedure, and the likelihood that the instruction insert 150 may be lost or separated from the corresponding testing devices is significantly minimized. In alternative configurations, the instruction insert may comprise, for example, but is not limited to, a bound booklet or individual cards that are separated from one another.

As shown in FIGS. 23-28, the pages of the instruction insert 150 may be easily flipped to provide a sequence of instructions, e.g., steps 1-7b, which guide the user through the entire testing procedure. As illustrated, the instruction insert 150 may also include separate sections that provide instructions according to one or more different languages, such as Spanish. With the upper surface 128 at an obtuse angle (e.g., 100-145 degrees, such as about 120 degrees) relative to the base 126, each page can be flipped over and stably positioned against the interior surface 132 of the upper surface 128. As such, two pages of the instruction insert 150 may be easily viewed at a time. Advantageously, the presentation of the instructions using a flip-book helps the user to follow the prescribed sequence of steps for the test.

Figure 23:
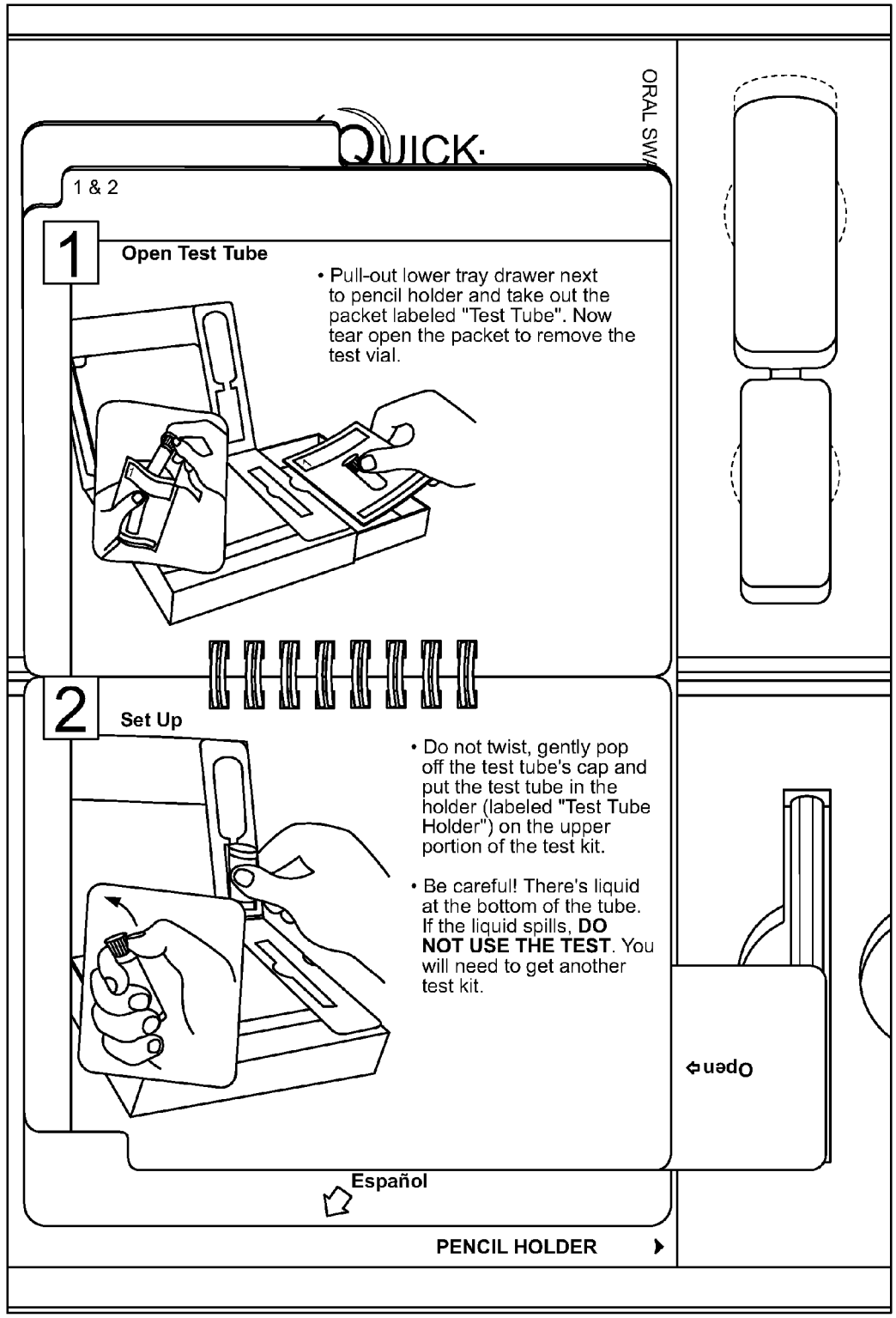
FIG. 23 illustrates an instruction insert in the testing container of FIG. 22, showing steps 1 and 2 for administering the corresponding testing system.

FIGS. 23-28 show a particular embodiment of the container 100, which provide instructions for an over-the-counter home HIV test, such as a version of the OraQuick® Rapid HIV-1 Antibody Test. The instructions provided here are presently merely as an example. Of course, different information and instructions may be provided by the instruction insert 150 corresponding to other types of testing procedures and testing devices. It should be appreciated that the multiplicity and complexity of components may require unique and specialized instructions. For example, referring to FIG. 23, step 1 in the instruction insert 150 prompts the user to pull out the tray 140 from the base 126 and remove the first packet 158 labeled "Test Tube." These instructions are provided not only textually, but are also advantageously graphically depicted, showing not only the physical removal of the first packet 158 from the tray 140, but also the required operation to be performed on the first packet, tearing open the first packet to retrieve the test vial. However, although clearly advantageous, the present concepts do not require the instructions to be provided in a graphical formal and such instructions may optionally only be textual. To facilitate compliance with the instructions and to make it clear to the user which item should be selected from the tray 140, the "Test Tube" packet 158 is preferably the first visible item in the tray 140. In other words, the sequence of presentation of the items in the tray 140 may advantageously correspond to the items designated sequence of use. As shown, the first packet 158 may provide a vial, or test tube, 160. FIG. 23 shows that the next step 2 in the instruction insert 150 instructs the user, both textually and graphically, to remove the cap 161 of the vial 160 and place the vial 160 in the recess 138B of the upper section 128.

Figure 24:
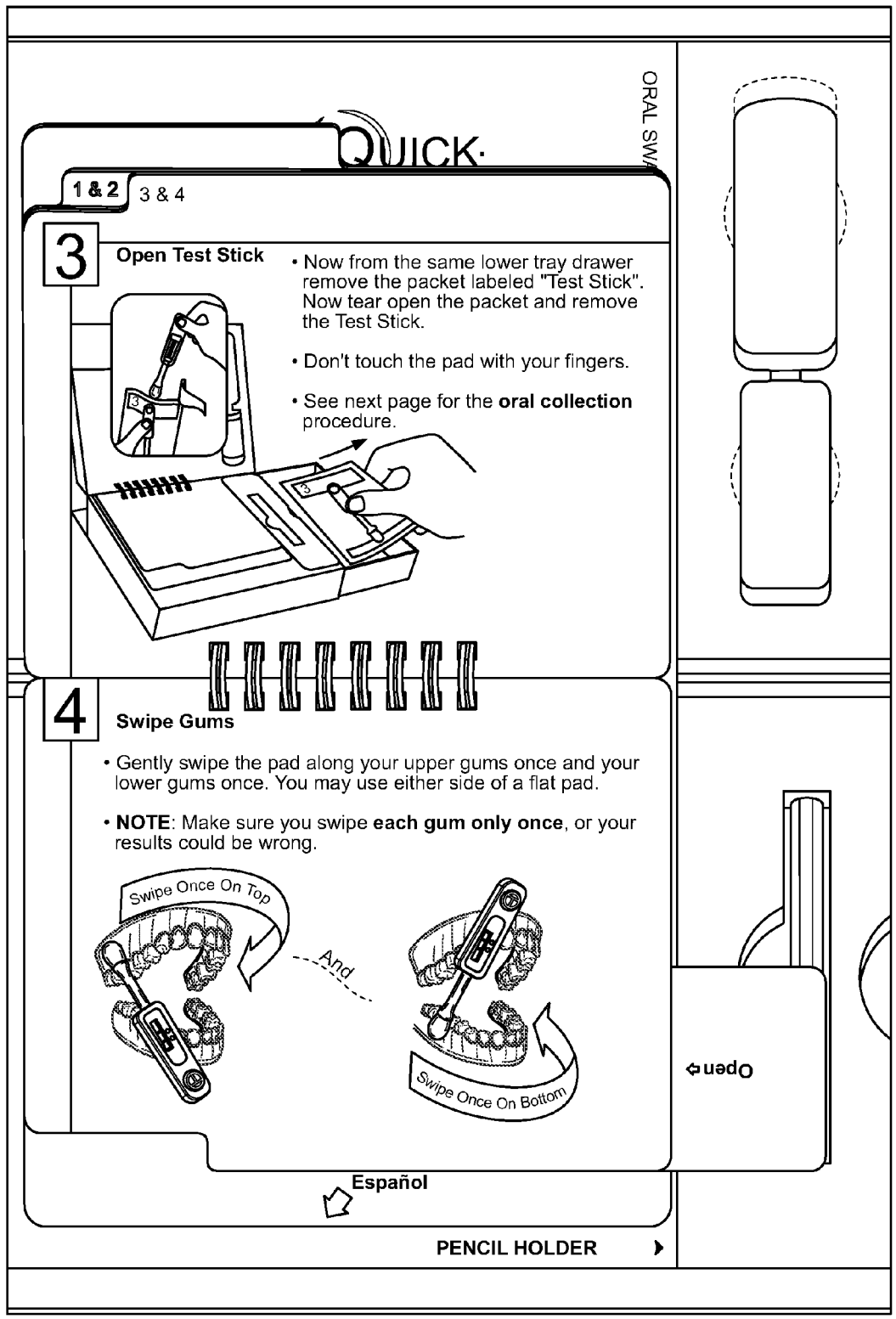
FIG. 24 illustrates the instruction insert of FIG. 23, showing steps 3 and 4 for administering the corresponding testing system.

As shown in FIG. 24, step 3 in the instruction insert 150 instructs the user, both textually and graphically, to remove the second packet 162 labeled "Test Stick" from the tray 140. As discussed previously, the items in the tray 140 may be advantageously organized according to the sequence in which they should be accessed, but this is not required by the present concepts. As such, the second packet 162 can be placed next to or underneath the first packet 158, or alternatively, it can be located within a separate compartment in the tray 140. Once the first packet 158 is removed in step 1, the second packet 162 is preferably, but not necessarily, the most visible item in the tray 140. In this example, the second packet 162 may contain an OraQuick® test stick device 170, which is removed by the user, applied as directed in FIG. 24 for use with the vial 160. As shown in FIG. 24, step 4 in the instruction insert 150 provides textual and graphical instructions on how to administer the test stick 170 to collect a sample for the test, e.g., swiping the user's gums with the test stick 170. Other types of tests may require use of other types of sampling devices to collect a sample from a user such as, but not limited to, a non-oral test stick or test strip. It also bears noting that, although the depicted examples of FIGS. 1-32 utilize a vial 160, other testing systems that may be used in accord with various aspects of the present concepts may advantageously omit such a second test component and a test stick or test device therein may itself provide a visual indication of the test result after lapse of an appropriate amount of time.

Figure 25:
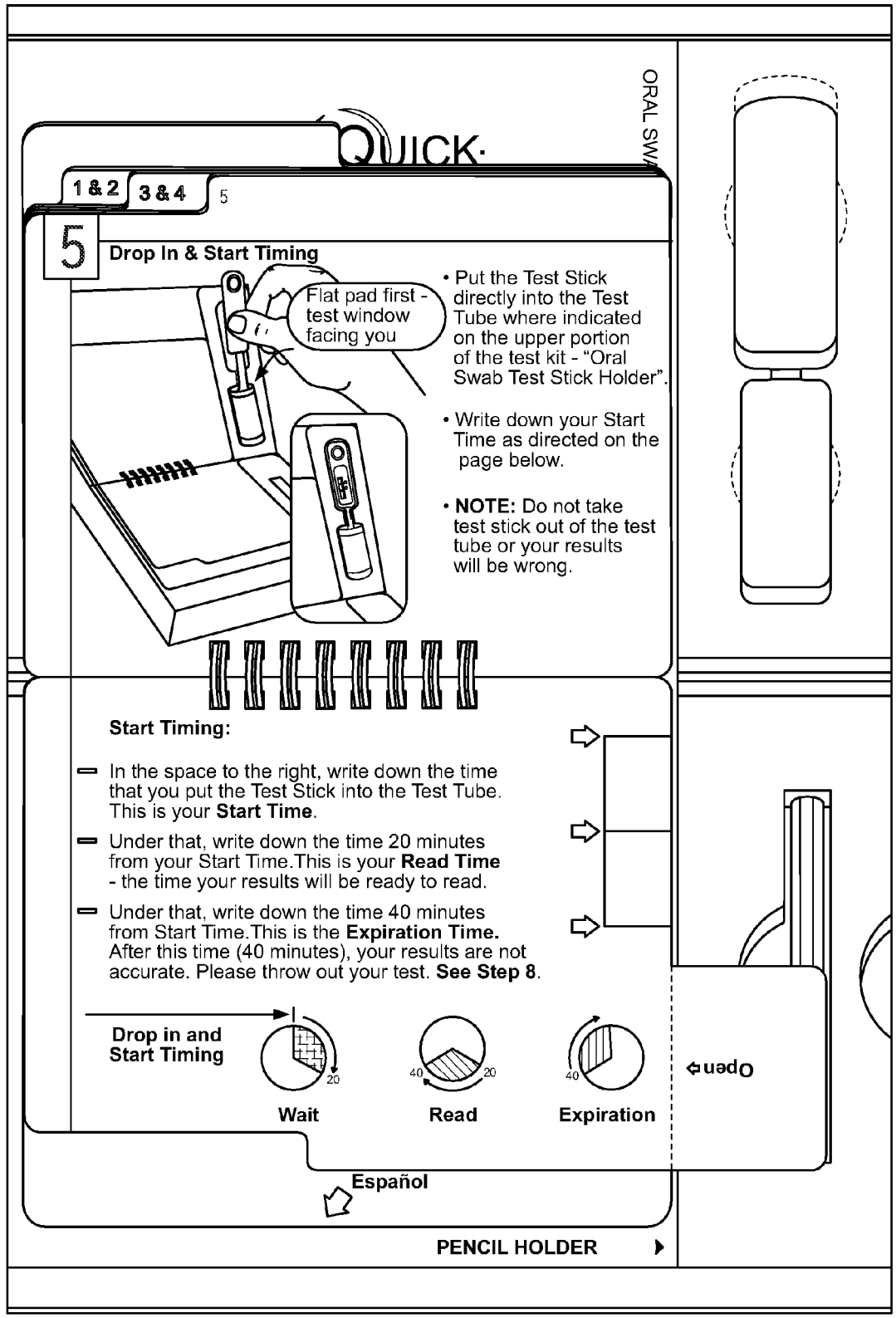
FIG. 25 illustrates the instruction insert of FIG. 23, showing step 5 for administering the corresponding testing system.
Figure 26:
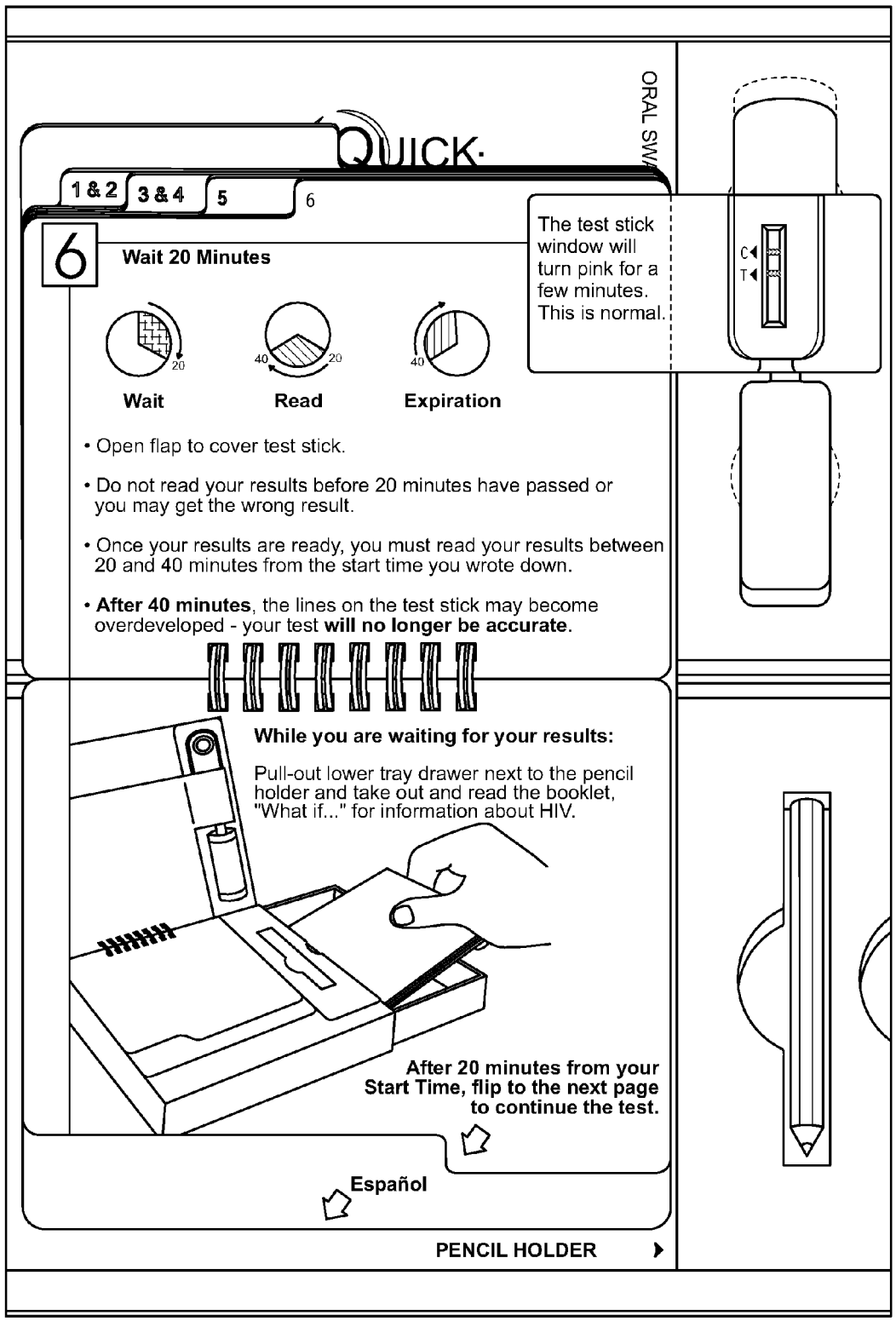
FIG. 26 illustrates the instruction insert of FIG. 23, showing step 6 for administering the corresponding testing system.
Figure 30:
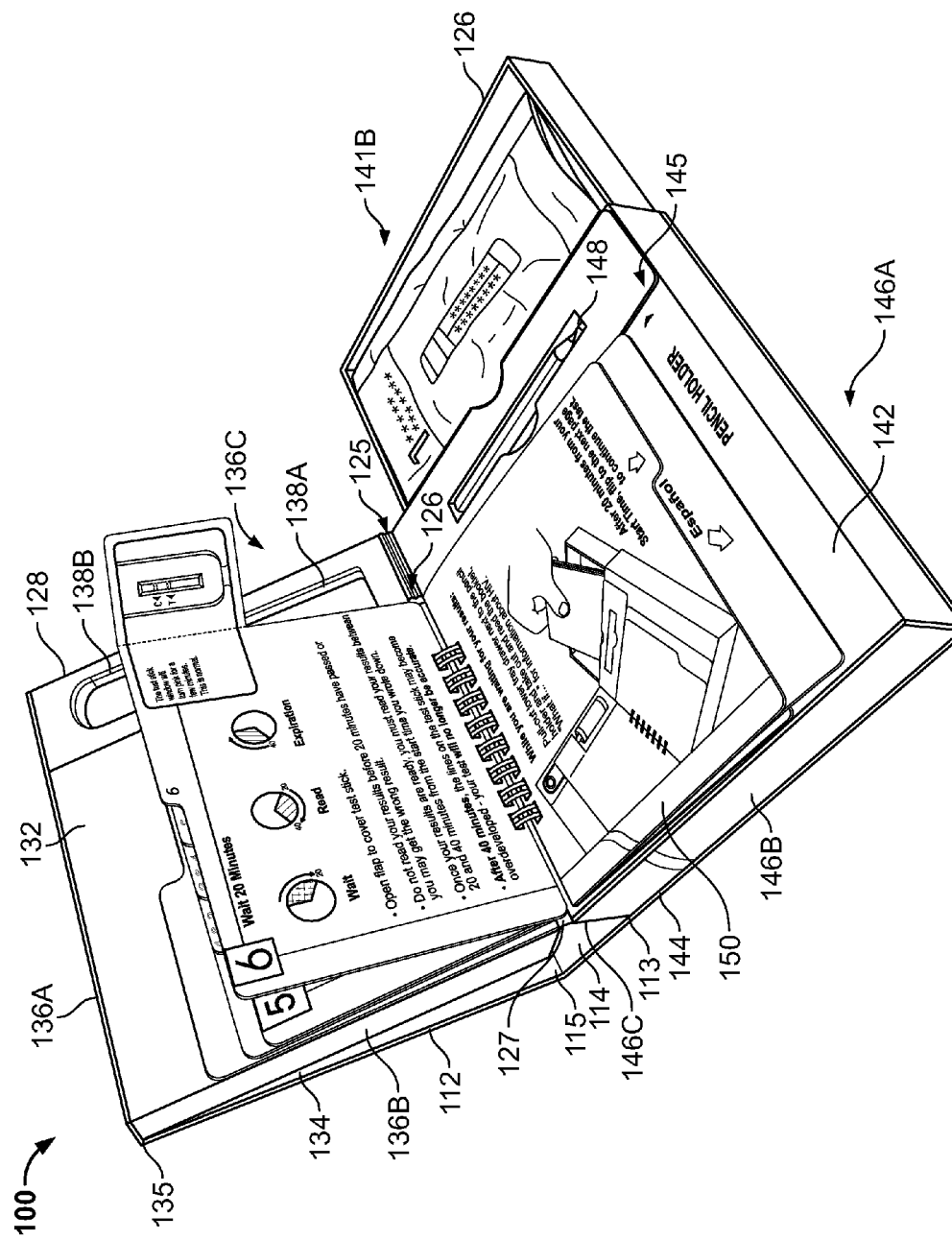
FIG. 30 illustrates the perspective view of the testing container of FIG. 29, showing the instruction insert being flipped to the page showing step 6.
Figure 31:
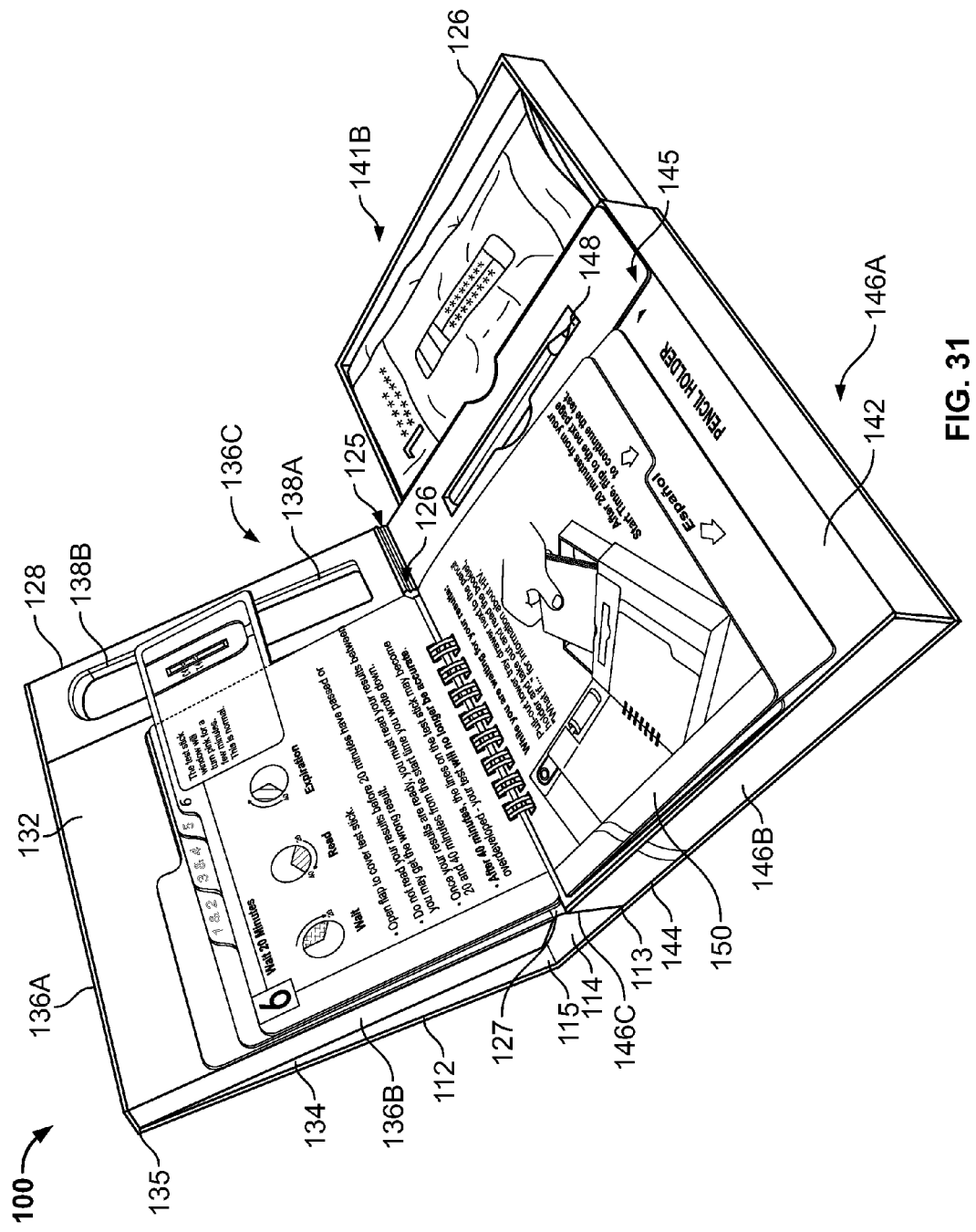
FIG. 31 illustrates the perspective view of the testing container of FIG. 29, showing the instruction insert flipped to the page showing step 6.

As shown in FIG. 25, step 5 instructs the user, via both textual and graphical instructions, to place the test stick 170 with the collected sample into the vial 160. The test stick 170 is now disposed in the vial 160, and the combination of the test stick 170 and the vial 160 are received into the recesses 138A and 138B, respectively. The user is then instructed to wait for the test results according to a specified time. In the illustrated example, the pencil 139 is provided in the recess 148 to allow the user to calculate and note the start and end times for the waiting period. The user may also be instructed to calculate an expiration time, which marks the point after which the test is no longer valid. As shown in FIGS. 30 and 31, when the page for step 6 is presented, an optional flap 166 covers the test stick 170 while the collected sample is being processed. This flap both provides useful information regarding the test indications and discourages the user from reading the results on the test stick before the required waiting period is complete. In addition, step 6 instructs the user to remove the first booklet 18A entitled "What if . . . " from the tray 140. This first booklet 18A may provide further information on the test and/or may prepare the user for the possible test results.

Figure 27:
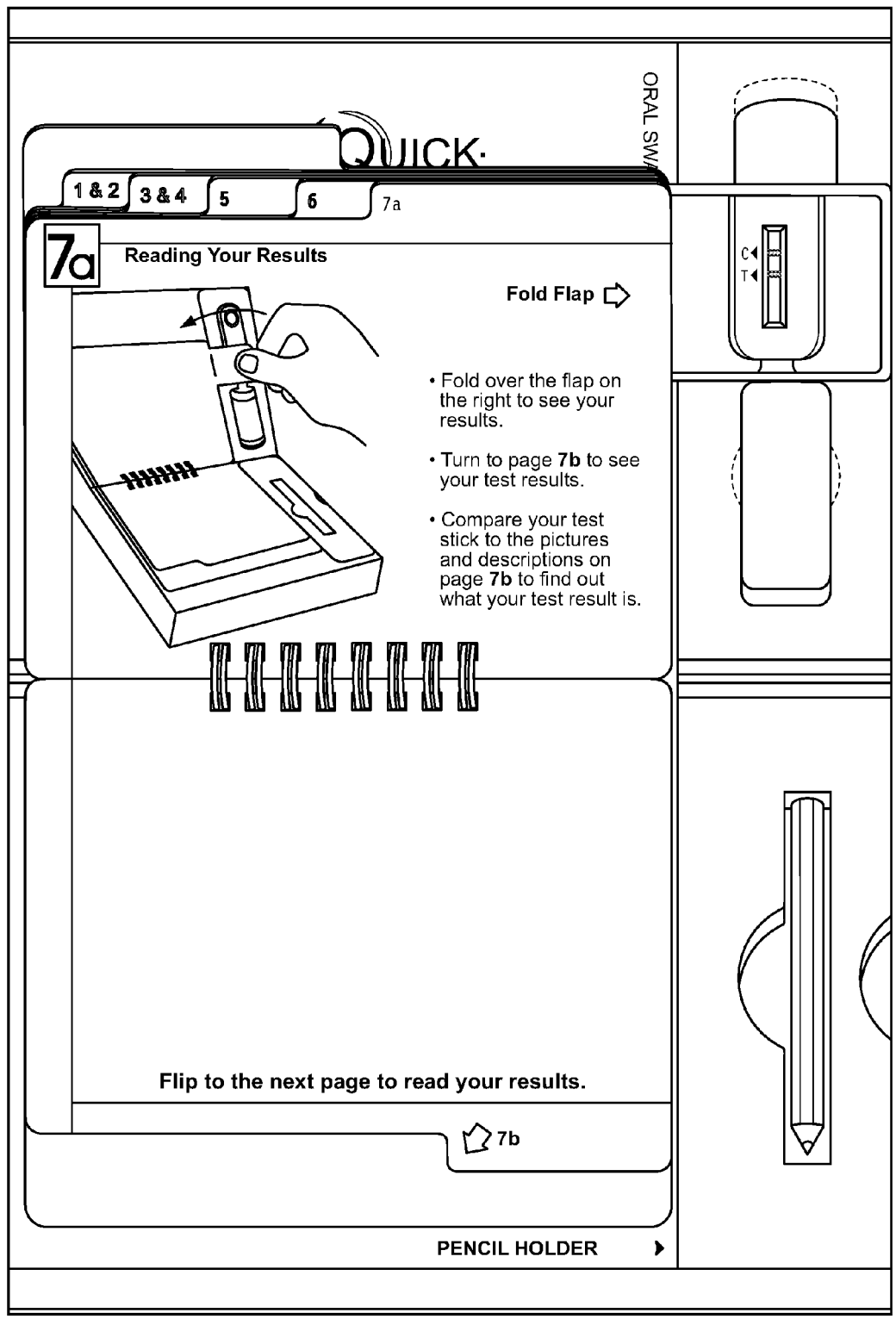
FIG. 27 illustrates the instruction insert of FIG. 23, showing step 7a for administering the corresponding testing system.
Figure 28:
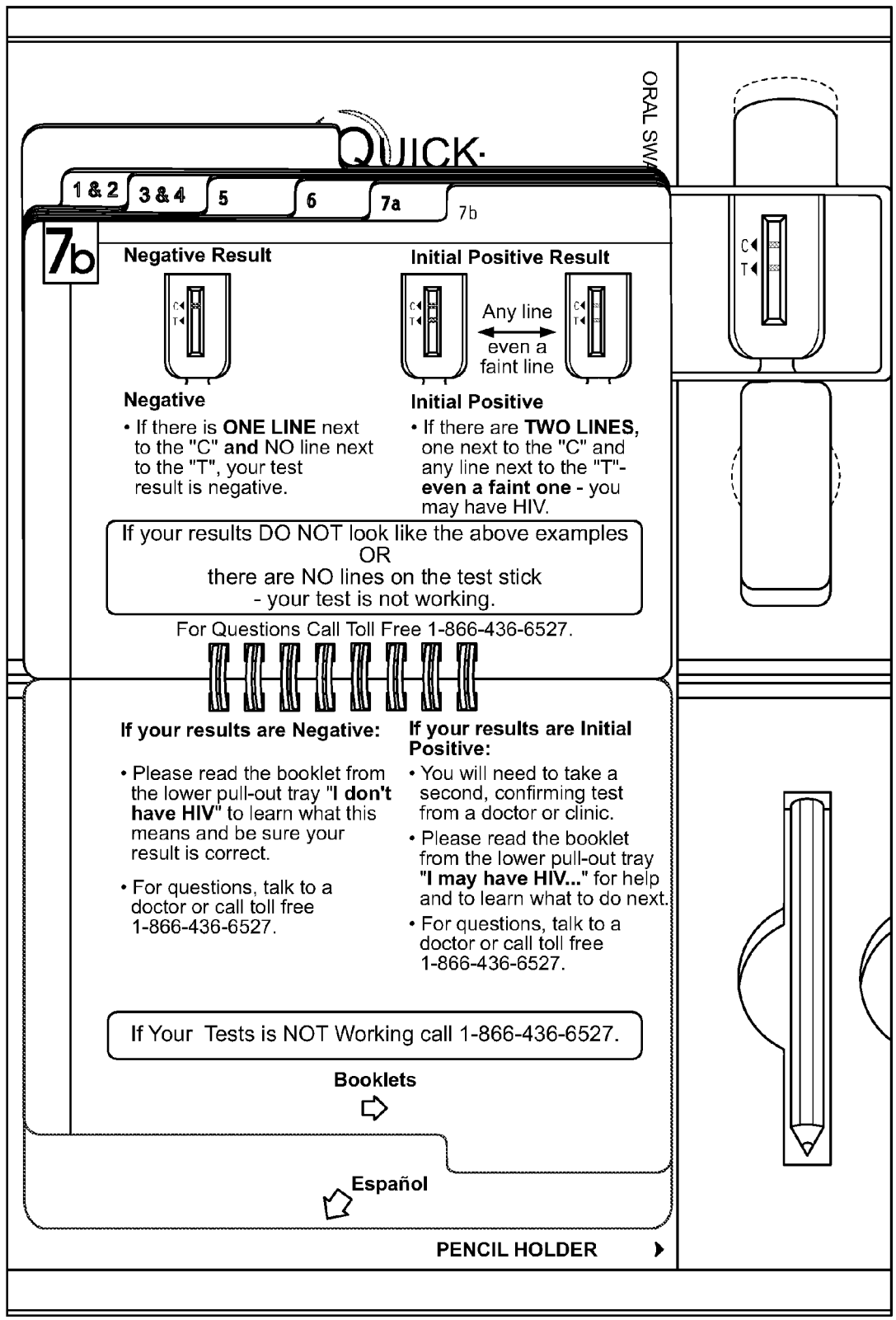
FIG. 28 illustrates the instruction insert of FIG. 23, showing step 7b for administering the corresponding testing system.

As shown in FIG. 27, at the end of the waiting period, step 7a instructs the user to remove tab 166 to view the test results and to determine if the result is negative, i.e., the HIV-1 and HIV-2 antibodies were not detected in the specimen, or positive, i.e., the HIV-1 and HIV-2 antibodies were detected in the specimen. Depending on the test result, as shown in FIG. 28, steps 7b and 7c instruct the user to remove, from the tray 140, either the pamphlet corresponding to a negative result or the pamphlet corresponding to the positive result.

As discussed previously, testing devices, such as the vial 160 and the test stick 170, are kept in packets 158 and 162. While these packets 158 and 162 can protect the integrity of the devices inside the packets 158 and 162, it may be desirable to provide further protection for the container 100. As such, the container 100 may be provided with an extra covering, such as shrink-wrap. Moreover, the container 100 may be provided with another outer box, which in turn may also be wrapped or covered. In addition to the added physical protection afforded by the packaging, such additional packaging components, such as shrink wrap, facilitate tamper detection.

The information provided with the method, device and/or packaging according to the invention may also include pre-test and post-test counseling options. The counseling is preferably confidential with the user contacting a counselor by phone, via a website, by a personal visit, etc. One type of home test kit with telephonic verification of results is described in U.S. Pat. No. 6,319,665, which is incorporated herein by reference in its entirety.

Pre-test counseling is designed to introduce and orient users to the rapid test and support the home testing users to identify individual circumstances and develop a personal action plan before the test. Pre-test counseling options may provide a step-by-step guide to users before taking a test. Pre-test counseling may include, for example, information relating to risk reduction of infectious diseases, evaluation of the user's behavioral or clinical risk assessment to infectious diseases, testing resources to choose the appropriate test method, access to existing prevention counseling, and introduction of the rapid testing process such as what to expect from the test and what the results may mean. The information may also inform users of available websites with education materials, e-mail address to contact, toll-free phone counselors to walk users through using the test, links to local counseling and public health resources, where to get pamphlets, how to make an appointment for a face-to-face meeting with trained and certified counselors, a call center available 24 hours and 7 days a week, etc.

Post-test counseling supports users by assisting with the interpretation of the test results and informing them of other services and assistance to evaluate the test result and initiate follow-up treatment and/or counseling. It would likely include that same information as pre-test counseling but post-test counseling may also provide information of on-going disease prevention and support services available for users with negative test result. In case the test result is negative or invalid, post-test counseling may provide information regarding public health services or a directory of local physicians who can assist home testing users. When the test result is positive, post-test counseling options provide users referral services by which they can immediately access to care and supportive services such as setting up appointments or providing transportation in assessing services. Post-test counseling options inform users with positive results how to receive or be referred to medical services that address, for example, their HIV infection to evaluate immune system function and screening, treatment, and prevention of opportunistic infections.

Although the above concepts have been described in relation to particular examples, many other variations and modifications and other uses will become apparent to those skilled in the art. For example, in lieu of the disclosed moveable tray 140, the base 126 may include another stationary lateral surface opposite surface 146B and access to the moveable tray provided through an opening where surface 146A is shown. Thus, the movement of the tray may be in a direction toward the user. In still another alternative configuration, the tray 140 itself may be stationary and access to the tray may be accomplished by hinging surface 142 relative to a sidewall 146B or 146C. Further, although the testing apparatus shown in the examples depicted an OraSure® Oral Specimen Collection Device FDA approved for the purpose of collecting, preserving, and transporting oral fluid specimens, the testing apparatus may comprise any test stick or testing device adapted to test for any desired virus, agent, marker, protein, chemical, biological material, non-biological material, or the like, suitable for purposes such as, but not limited to, substance abuse testing, infectious disease testing, toxicology, insurance testing, plasma screening. Thus, for example, the present concepts may be used in combination with an OraQuick ADVANCE® HIV-1/2 Antibody Test, an FDA approved test than can be used on oral fluid, plasma, fingerstick and venipuncture whole blood specimens, or with the OraSure® MICRO-PLATE drug tests used in forensic toxicology to analyze blood, urine, hair, oral fluid, sweat, and other forensic samples. Likewise, the present concepts may be advantageously utilized in combination the OraSure® EIA test kits (e.g., MICRO-PLATE and AUTO-LYTE®) for risk assessment testing of life insurance applicants and screen for drugs of abuse, nicotine use, and therapeutic drugs.

In accord with still additional variants of the present concepts, the disclosed tray 140 may itself comprise a plurality of separate compartments, each compartment housing a corresponding article for use in the test. Each compartment may be designated, further to any graphical representation present in the instructions, whether provided in the instruction insert 150 or elsewhere, additional graphical indicators, such as color and/or number. Thus, the tray may include a plurality or articles, each article borne by a numbered and/or colored compartment (e.g., the color, if any, may correspond to a background color or border color of a corresponding instruction in the instruction insert).

The present concepts include, as noted above, pre-test and post-test counseling options, which are described in more detail below. As described herein, "counseling system" or "counseling" includes, but is not limited to, services available to a consumer via a toll free number and/or the internet, which may include full-service HIV/AIDS prevention and treatment counseling from OraSure or other designated party. These options go beyond merely providing to a user technical support for the device, basic HIV/AIDS information, and/or referrals to other appropriate providers for counseling and other care.

As described in relation to the above examples, relating to FIGS. 1-32, at least some aspects of the present concepts concern a system and method for home testing and diagnosis of infectious diseases including, but not limited to, HIV and hepatitis C using OraSure's OraQuick® device. The information provided to a user may advantageously include, further to the noted instructions on use, pre-testing counseling options and/or post-testing counseling options upon the occurrence of a positive test result.

Pre-testing counseling options include, but are not limited to, information concerning risk reduction of infectious diseases, evaluation of home test user's behavioral or clinical risk assessment to infectious diseases, testing resource directory to choose the appropriate test method, access to existing prevention counseling, and introduction of the rapid testing process such as what to expect from the test and what results means. The information may also provide home testing users available websites with education materials, e-mail address to contact, 1-800-numbers to walk through home test users during the test, links to local counseling and public health resources, "where to get" pamphlets, how to make an appointment for a face-to-face meeting with trained and certified counselors, and a call center available 24 hours and 7 days a week. Pre-testing counseling options are designed to introduce and orient home testing users to the rapid test and to support the home testing user in identifying individual circumstances pertinent to the user and to develop a personal action plan before the test.

The user instructions support home testing users by providing the step-by-step directions for use of the article or goods inside the container. The user instructions include instructions concerning test preparation and reading of test results, as is shown by way of example in FIGS. 23-28.

As to the reading of the test results, in one aspect of the present concepts, a test is negative if a reddish-purple line appears next to the triangle labeled "C", and no line appears next to the triangle labeled "T" within an appropriate "read" time for the sample (see FIG. 28). A negative test result means that HIV-1 and HIV-2 antibodies were not detected in the specimen. A test is positive if a reddish-purple line appears next to the triangle labeled "C" and a reddish-purple line appears next to the triangle labeled "T" within an appropriate "read" time for the sample. In some aspects, the test is positive if any reddish-purple line appears next to the "T" triangle and next to the "C" triangle, no matter how faint these lines are. A positive test results means that HIV-1 and HIV-2 antibodies have been detected in the specimen and the user is then directed to the post-testing counseling options.

Post-testing counseling options support home testing users informing other services and assistance to evaluate the test result and initiate follow-up counseling. Post-testing counseling options may provide information of on-going HIV prevention and support services available for home testing users with negative test result. In case the test result is invalid, after-testing counseling options may have information of public health service or local physician directory who can assist home testing users for repeated testing. When the test result is positive, after-testing counseling options provide home testing users referral services by which home testing users immediately can access to care and supportive services such as setting up appointments or providing transportation in assessing services. Referral services may include toll-free telephone number available 24 hours 7 days a week, contact information of local public health department, local health care physician's directory, available websites with interactive features or e-mail address to contact. Post-testing counseling options inform home testing users with positive result to receive or be referred to medical services that address their HIV infection to evaluate immune system function and screening, treatment, and prevention of opportunistic infections.

In at least some aspects of the present concepts, the counseling system includes an inquiry module used by counselors to record inquiry activity, a response module used by content authors to maintain the call scripts, and a module for other required functionality, which may relate particularly to website, email, contingency plans, and security issues.

The inquiry module will capture and report general call center metrics (e.g., date and time of call, call duration, answered by whom, hold times, wait times, etc.), non-identifying caller information (e.g., language spoken, frame of mind, zip code, other inferred data such as gender and age group, study ID number during trial, etc.), call basis (e.g., reason for calling, such as device problems, needing HIV information and/or referral, complaints, etc.), and resolution of inquiries (e.g., referrals made, tech support provided, escalation, etc.).

Call center metrics are useful for reporting and statistical functions, as well as for process improvements. Call center metrics may include, for example, call counts (e.g., by day, by time of day, by month, by language, by call type, for a given date range, by counselor, etc.), call duration (e.g., average, maximum, minimum, by call type, by language for a given date range, by counselor, etc.), and/or hold times (e.g., average, maximum, minimum, by call type, by language for a given date range, etc.). Reporting capability is further enhanced by documenting of other metrics including caller information (e.g., call counts by language, frame of mind, zip code or state, by gender and age group, etc.), calls by topic (e.g., average, maximum, minimum, by language for a given date range, etc.), as well as counts of actions taken or recommended (e.g., by language, frame of mind, zip code or state, by gender and age group, etc.).

Figure 33:
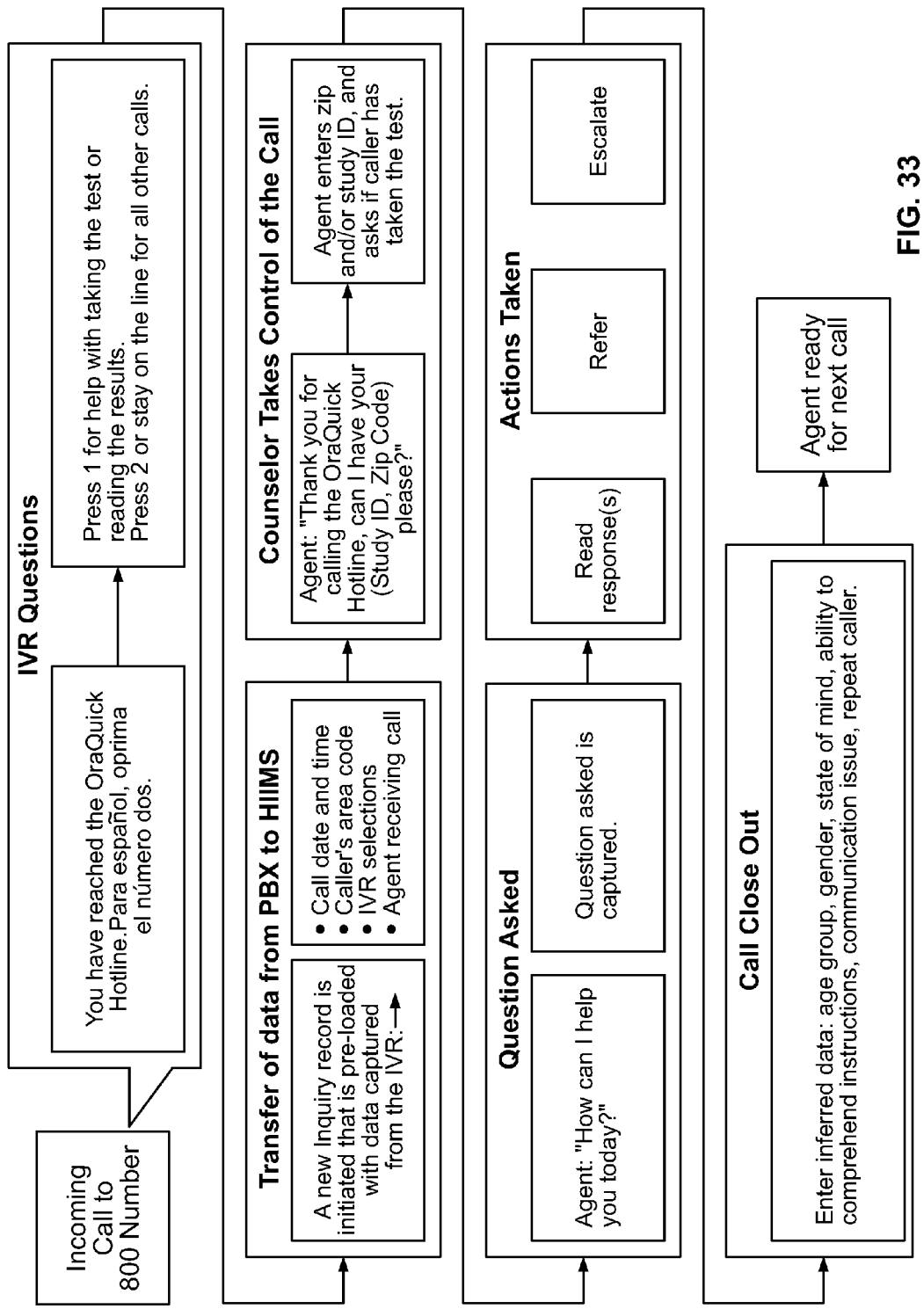
FIGS. 33-34 illustrate aspects of a counseling method in accord with at least some aspects of the present concepts.

FIG. 33 shows one representation of a process for an inquiry module. Responsive to an incoming call to a toll-free number, an interactive voice response system (IVR) notifies the caller of the nature of the toll-free number (e.g., the OraQuick hotline) and queries the caller. As shown in FIG. 33, the call is asked to "Press 1 for help with taking the test or reading the results" or to "Press 2 or stay on the line for all other calls." Following this initial screening, the caller's data is transferred from the private branch exchange (PBX) to an intelligent infrastructure management system (IIMS), wherein a new inquiry record is initiated that is pre-loaded with data captured from the IVR including, but not limited to, call date and time, caller's area code, IVR selections, and/or the agent receiving the call. The call is then passed to the counselor, who takes control of the call. Advantageously, the counselor may operate from a prepared script. As shown in FIG. 33, the counselor states "Thank you for calling the OraQuick Hotline, can I have your (Study ID, Zip Code) please?" upon which response the counselor enters the caller's zip code and/or study ID, and asks if caller has taken the test. The counselor then asks the caller "How can I help you today?" and documents the caller's question or request. Follow-up actions are then taken by the counselor to read the response(s) relevant to the caller's question from the prepared script, which comprise a physical script or a script presented on a display, and may take further actions as indicated by such script, such as referring the caller to a designated individual, group, or resource or to escalate the call to a counselor having greater knowledge and/or authority or to any other designated individual, group, or resource. Escalations may include, for example, crisis referrals to 911 or suicide prevention hotlines. Following completion of such actions by such counselor, the counselor then closes out the call, entering any inferred data, such as but not limited to age group, gender, state of mind, ability to comprehend instructions, communication issue, repeat caller, etc.

Figure 34:
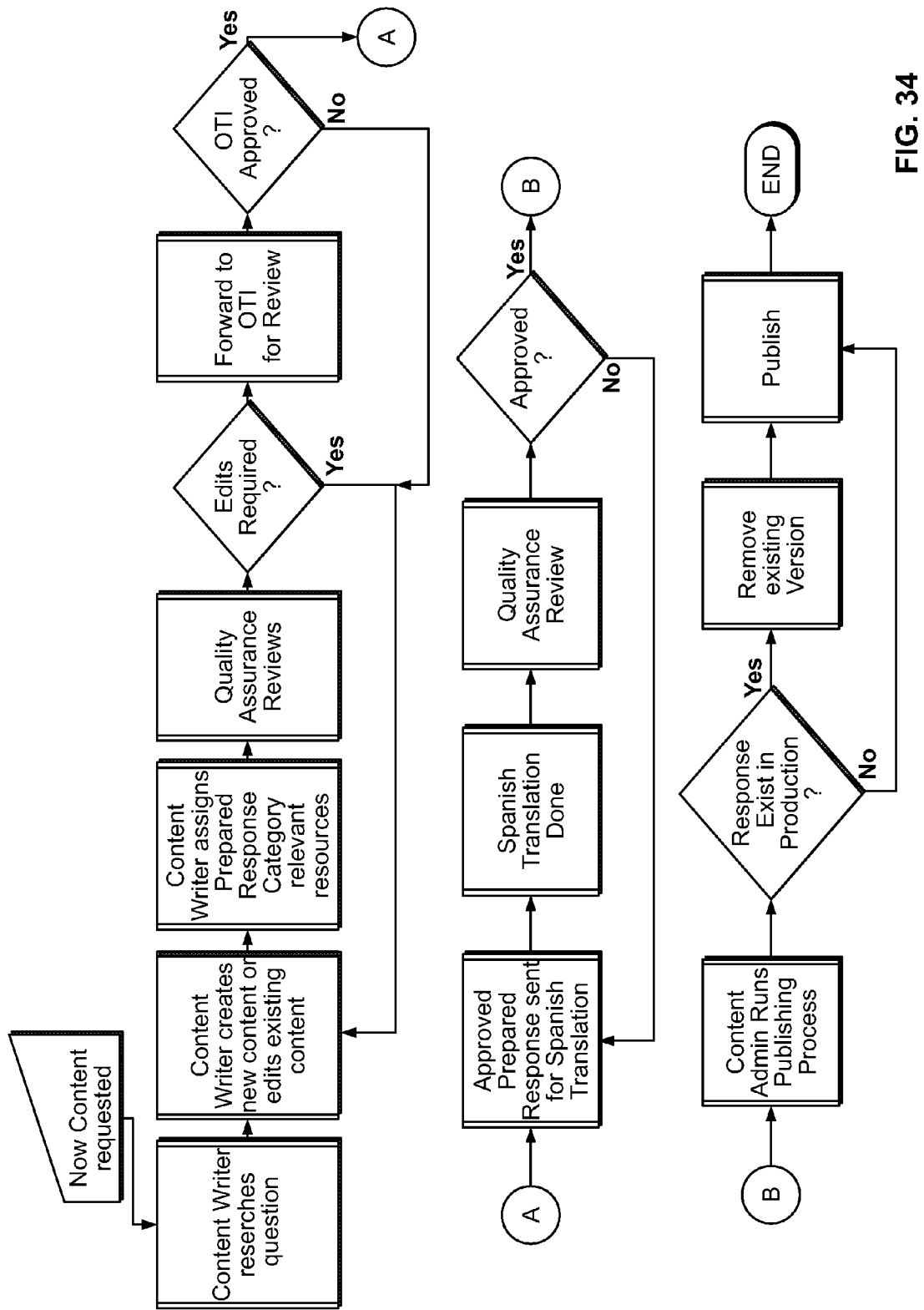

One example of aspects of a response module are represented in FIG. 34. The response module provides the means for content authors to create, edit, and review the scripts that are used to answer call center inquiries. In accord with the illustrated example, the workflow is driven by status codes that indicate each step of the content lifecycle. Once approved and in use by the call center, further edits to the response are made in an "In Process" copy of the response. The production version remains untouched and static until the newer version completes the editing process. Categories and keywords for search and reporting advantageously include response type, which includes tech support for device assistance, model language for help with HIV/AIDS issues, referral for counseling, and customer service. The main portion of the script is the "Question and Answer" that is used by the counselor to address any questions or issues raised by a caller. Each Question and Answer advantageously includes "related responses," "background info," and "call to action" sections, to facilitate prompt answering of not only a caller's immediate inquiry, but also related inquiries, with appropriate pointers to the counselor to transition into more detailed treatments of such related inquiries. For example, the script may link responses when one topic relates to another such as by linking responses to questions regarding transmission to response to related questions about a potential window of infection. The scripts may include, for example, related publications and resources available to the caller, such as those that may be available on-line. The response module also desirably includes an audit trail for each record, so that the system will track who changed the record, when it was changed, and the nature of the changes, if not detailed information on each change.

Turning to FIG. 34, responsive to a request for new content, from whatever source, a content writer is tasked to research the question. Responsive to this research, the content writer then creates new content or simply edits the existing content. The content writer also assigns the new or revised content a prepared response category, if needed, together with additional of supplemental information (e.g., relevant resources, etc.), which is followed by a quality assurance review and identification of any needed edits. If additional edits are required, the process then passes back to the content writer creates new content or edits existing content as required by the edits requested by the quality assurance review. At the point where no edits are required, the new or revised content is then forwarded to a reviewing authority for final substantive review and approval. Following final substantive review and approval, the approved content is then sent for translation into one or more additional languages (e.g., Spanish), which is then reviewed by quality assurance to ensure accuracy, and approved if warranted. Following any required translations, a content administrator runs the completed new content or revised content through publishing. If the content is new content, such new content is then added into the production or "in process" scripts or, if the content is revised content of already existing content, the existing version of the script corresponding to the revised content is removed and replaced with the revised content.

As noted above, users of the testing kit may advantageously be directed to a website where the user may obtain information and/or counseling. In some aspects, the website may include graphics of the test instructions (e.g., instruction packet 150), video demonstrations, video and/or audio and/or textual testimonials, additional instructions or booklets in a variety of languages, frequently asked questions (FAQs) for device-related questions, FAQs for general HIV/AIDS and testing information, information for contacting a customer service number, and links to other websites. Optionally, although not presently preferred, a visitor to the website may be permitted to complete an email form to submit a question. At the present time, it is preferred that email options be limited to outbound (one-way communication) only, but this is not a requirement. As to outbound emails, a counselor may provide information to a caller's request in a simple, text only, resource and publication links, addresses for referrals, and/or attachments in PDF format.

Referrals for care are advantageously documents by organization name and address and may by automatically populated or manually entered by a counselor. Referrals for care may comprise a search of existing websites maintained by CDC and their vendors and links available from the response and/or inquiry pages of the scripts. In some aspects, therefore, the CDC organizational data is uploaded and indexed and mated with an engine permitting a radius or geography-based search that may also automatically capture data about a selected referral (e.g., the name and type of organization, address, contact information, etc.).

Functionality may be provided for call backs. For example, a caller may be provided with a reference number that may be later provided to the same or another counselor to enable that counselor to look up the caller's service record. This system preserves caller confidentiality.

Although the above concepts have been described in relation to particular examples, many other variations and modifications and other uses will become apparent to those skilled in the art and are covered at least in part by the appended claims.

What is claimed is:

1. A method of sequentially accessing test devices located within a testing kit as sequentially indicated to perform a test and determine a test result, the method comprising:
   opening a container, said container including:
      an upper portion having at least one receiving space interior to said upper portion and configured to receive a combination of a first test device and a second test device and further configured to hold the combination of a first test device and a second test device in a testing position during a test;
      a lower portion connected to said upper portion, said lower portion defining an interior space,
      an instructional insert disposed between said upper portion and said lower portion;
      a moveable tray disposed in said interior space of said lower portion, and
      a first test device disposed in said movable tray and configured to receive a second test device;
      a second test device configured to be disposed in said first test device to form said combination of the first test device and the second test device;
   accessing at least one instruction from said instructional insert;
   accessing said movable tray based on said at least one instruction from said instructional insert;
   sequentially positioning said instructional insert to gain sequential access to said first test device disposed in said movable tray;
   accessing said second test device disposed in said movable tray in correspondence to said at least one instruction from said instructional insert;
   performing a testing act directed by said at least one instruction from said instructional insert utilizing at least one of said first test device or said second test device disposed in said movable tray in correspondence to said at least one instruction from said instructional insert;

disposing said second test device in said first test device to form said combination of the first test device and the second test device;

positioning said combination of the first test device and the second test device in said receiving space in said testing position; and determining a test result based upon said testing act.

2. The method of claim 1, wherein accessing at least one instruction from said instructional insert comprises accessing both textual and graphical instructions.

3. The method of claim 1, wherein said combination of the first test device and the second test device is a testing device for the testing and diagnosis of a predetermined infectious disease.

4. The method of claim 1, further comprising:

sequentially accessing a plurality of instructions from said instructional insert;

sequentially accessing said first test device and said second test device disposed in said movable tray in correspondence to said instructions from said instructional insert; and sequentially performing acts directed by said plurality of instructions from said instructional insert utilizing said first test device and said second test device in correspondence to said plurality of instructions from said instructional insert.

5. The method of claim 1, further comprising:

interpreting said test result in accord with said at least one instruction from said instructional insert.

* * * * *